United States Patent
Hunt, III et al.

(10) Patent No.: US 10,059,660 B2
(45) Date of Patent: *Aug. 28, 2018

(54) SOLID DRUG FORM OF N-(2,6-BIS(1-METHYLETHYL)PHENYL)-N'-((1-(4-(DIMETHYLAMINO)PHENYL)CYCLOPENTYL)METHYL)UREA HYDROCHLORIDE AND COMPOSITIONS, METHODS AND KITS RELATED THERETO

(71) Applicant: Millendo Therapeutics, Inc., Ann Arbor, MI (US)

(72) Inventors: Stephen Warren Hunt, III, Dexter, MI (US); Martin Douglas Phillips, Bryn Mawr, PA (US); Robert Matunas, East Windsor, NJ (US); Herman Chen, Madison, CT (US); Aimesther Betancourt, Montréal (CA); Charles Uzarama, Laval (CA); Roch Thibert, Ville Mont-Royal (CA)

(73) Assignee: Millendo Therapeutics, Inc, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/370,980

(22) Filed: Dec. 6, 2016

(65) Prior Publication Data
US 2017/0305843 A1 Oct. 26, 2017

Related U.S. Application Data

(63) Continuation of application No. 14/866,212, filed on Sep. 25, 2015, now Pat. No. 9,546,135.
(Continued)

(51) Int. Cl.
*A61K 9/50* (2006.01)
*C07C 275/28* (2006.01)
(Continued)

(52) U.S. Cl.
CPC .......... *C07C 275/28* (2013.01); *A61K 9/2018* (2013.01); *A61K 9/2054* (2013.01);
(Continued)

(58) Field of Classification Search
CPC ........................... A61K 9/5084; A61K 9/2081
See application file for complete search history.

(56) References Cited

U.S. PATENT DOCUMENTS

| | | |
|---|---|---|
| 5,015,644 A | 5/1991 | Roth et al. |
| 2013/0267550 A1 | 10/2013 | Hammer et al. |

FOREIGN PATENT DOCUMENTS

| | | |
|---|---|---|
| JP | 2005/068066 A1 | 3/2005 |
| WO | 2013142214 A | 9/2013 |

OTHER PUBLICATIONS

Knölker et al., "A Novel Method for the Synthesis of Isocyanates Under Mild Conditions," *Angewandte Chemie. International Edition*, vol. 34, No. 22, pp. 2497-2500, Dec. 1, 1995.
(Continued)

*Primary Examiner* — Carlos A Azpuru
(74) *Attorney, Agent, or Firm* — Seed IP Law Group LLP

(57) ABSTRACT

A novel solid drug form of N-(2,6-bis(1-methylethyl)phenyl)-N'-((1-(4-(dimethylamino)phenyl)cyclopentyl)methyl) urea hydrochloride (also referred to "ATR-101") suitable for oral dosing, and to compositions, methods and kits relating thereto. ATR-101 has particular utility in the treatment of, for example, aberrant adrenocortical cellular activity, including adrenocortical carcinoma (ACC), congenital adrenal hyperplasia (CAH) and Cushing's syndrome.

6 Claims, 9 Drawing Sheets

Related U.S. Application Data

(60) Provisional application No. 62/055,964, filed on Sep. 26, 2014, provisional application No. 62/086,153, filed on Dec. 1, 2014.

(51) Int. Cl.
*C07C 273/18* (2006.01)
*A61K 9/20* (2006.01)
*A61K 31/17* (2006.01)

(52) U.S. Cl.
CPC .......... *A61K 9/2059* (2013.01); *A61K 9/2081* (2013.01); *A61K 9/5084* (2013.01); *A61K 31/17* (2013.01); *C07C 273/1809* (2013.01); *C07C 2601/08* (2017.05)

(56) References Cited

OTHER PUBLICATIONS

Rasenack et al., "Micron-Size Drug Particles: Common and Novel Micronization Techniques"; *Pharmaceutical Development and Technology*, vol. 9:1, pp. 1-13, Jan. 1, 2004.

Samardjiev et al., "2,6-Diisopropylanilinium Chloride," *Acta Crystallographica Section E. Crystal Structure Communications*, vol. 64, No. 8, pp. 112-o1480, Jul. 12, 2008.

Trivedi et al., "Inhibitors of acyl-CoA:Cholesterol Acyltransferase (ACAT) 7. Development of a Series of Substituted N-Phenyl-N-[(1-phenylcyclopentyl)methyl]ureas with Enhanced Hypocholesterolemic Activity" *J. Med. Chem.* vol. 37:11 pp. 1652-1659, May 27, 1994.

Vernetti et al., "ATP Depletion is Associated with Cytotoxicity of a Novel Lipid Regulator in Guinea Pig Adrenocortical Cells," *Toxicology and Applied Pharmacology, Academic Press*, Amsterdam NL. vol. 118, No. 1, pp. 30-38 Jan. 1, 1993.

SOLID DRUG FORM OF N-(2,6-BIS(1-METHYLETHYL)PHENYL)-N'-((1-(4-(DIMETHYLAMINO)PHENYL) CYCLOPENTYL)METHYL)UREA HYDROCHLORIDE AND COMPOSITIONS, METHODS AND KITS RELATED THERETO

CROSS REFERENCE TO RELATED APPLICATION

This application claims the benefit under 35 U.S.C. § 119(e) to U.S. patent application Ser. No. 14/866,212 filed Sep. 25, 2015, and to U.S. Provisional Application No. 62/055,964 filed on Sep. 26, 2014, and to U.S. Provisional Application No. 62/086,153 filed on Dec. 1, 2014, all of which applications are incorporated by reference herein in their entirety.

BACKGROUND

Technical Field

This invention relates to a novel solid drug form of N-(2,6-bis(1-methylethyl)phenyl)-N'-((1-(4-(dimethylamino)phenyl)cyclopentyl)methyl)urea hydrochloride (referred to herein as "ATR-101"), as well as to compositions, methods and kits relating to the same.

Description of the Related Art

The adrenal gland is made up of two parts: the outer cortex in which certain hormones are produced, and the inner medulla which is part of the nervous system, wherein nervous system hormones are produced. The cortex is devoted to the synthesis of glucocorticoid, mineralocorticoid and androgen hormones. Specific cortical cells produce particular hormones including aldosterone, cortisol, and androgens such as androstenedione. Adrenocortical tumors originate in the cortex.

There are two main types of adrenal cortex tumors: adenomas which are benign and adrenocortical carcinomas which are malignant. Adenomas in many people produce no symptoms, but in some instances the tumors lead to excess hormone production. Adrenocortical carcinoma can produce the hormones cortisol, aldosterone, estrogen, or testosterone, as well as other hormones. Adrenocortical carcinomas (ACC) are rare, highly malignant tumors. The tumor often releases these hormones, which in women can lead to male characteristics. The excess hormones may or may not cause symptoms. In general, adenomas are treated by removal of the adrenal gland or with therapeutic intervention. Likewise, adrenocortical carcinomas can lead to hormone production that can cause noticeable body changes such as weight gain, fluid build-up, early puberty in children, or excess facial or body hair in women. While the cause is unknown, adrenocortical carcinoma is most common in children younger than 5 and adults in their 30s and 40s. Adrenocortical carcinoma may be linked to a cancer syndrome that is passed down through families (inherited). Both men and women can develop this tumor.

While the understanding of the disease has advanced with the advent of modern molecular techniques, the prognosis of patients with advanced disease, who represent about half of the diagnoses, remains dismal. Targeted therapies are in clinical development, but whether they will yield breakthroughs in the management of the disease is yet unknown (Hammer, G. D. and T. Else, eds., *Adrenocortical Carcinoma, Basic Science and Clinical Concepts*, 2011, New York: Springer).

The sole FDA-approved therapeutic agent for ACC is mitotane (o,p'-DDD), a derivative of the insecticide DDT, discovered in 1950s, when it was found to destroy the adrenal cortex of dogs. Despite half a century of use, its molecular mechanism remains unclear. The drug requires chemical transformation into an active, free radical form, which then induces lipid peroxidation and cell death. Mitotane also suppresses steroidogenesis and inhibits other cytochrome P450-class enzymes (Id.).

Whereas mitotane is widely used for the treatment of ACC, it has increased progression-free survival in only one-quarter to one-third of patients. For the patients that derive a therapeutic benefit, the effect is transient, delaying disease progression by an average of five months (Id.). Mitotane has numerous problems as a therapeutic agent, making its use difficult, and requiring close monitoring of patients.

Accordingly, there remains a significant need for new therapeutic agents useful for treatment of ACC and other related diseases or conditions. One such promising agent is N-(2,6-bis(1-methylethyl)phenyl)-N'-((1-(4-(dimethylamino)phenyl)cyclopentyl)methyl)urea hydrochloride ("ATR-101"). The free base form of ATR-101 has the following chemical structure:

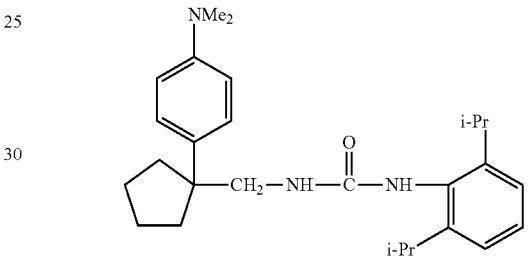

The chemical synthesis of ATR-101 has been previously reported by Trivedi et al. (J. Med. Chem. 37:1652-1659, 1994). This procedure, however, does not provide for ATR-101 in a form suitable for solid-dosing, particularly with regard to capsule or tablet formation, and does not provide for ATR-101 in high purity.

While significant advances have been made in this field, particularly in the context of ATR-101, there remains a substantial need for improved techniques and products for the oral administration of ATR-101 to patients in need thereof, including patients having ACC and/or other disorders or conditions such as Cushing's syndrome and congenital adrenal hyperplasia (CAH).

BRIEF SUMMARY

The present invention generally provides a novel solid drug form of N-(2, 6-bis(1-methylethyl)phenyl)-N'-((1-(4-(dimethylamino)phenyl)cyclopentyl)methyl)urea hydrochloride (referred to herein as "ATR-101"), as well as to compositions, methods and/or kits for oral administration of the same.

ATR-101 has particular utility in the treatment of aberrant adrenocortical cellular activity, including ACC and other conditions as described in greater detail below. The solid drug form of ATR-101 provided herein provides for for high loading capacity, thus allowing formulation of ATR-101 in a form suitable for oral dosing.

In an embodiment, a solid drug form of ATR-101 is provided having a particle size distribution as follows: d(0.1) of about 2 μm, d(0.5) of about 12 μm, and a d(0.9) of about 49 μm.

In an embodiment, a solid drug form of ATR-101 is provided having a differential scanning calorimetry (DSC) onset at about 228.28° C. and endotherm at about 230.93° C.

In an embodiment, a solid drug form of ATR-101 is provided having a purity in excess of any one of the following values: 95% (w/w), 96% (w/w), 97% (w/w), 98% (w/w) and 99% (w/w).

In an embodiment, an oral dosage product is provided comprising a solid drug form of ATR-101, such as a capsule, tablet or pill.

In a embodiment, a solid pharmaceutical composition is provided in a unit dosage form suitable for oral administration. The composition comprises ATR-101 in combination with one or more pharmaceutically acceptable carriers or excipients, wherein ATR-101 is present in the solid pharmaceutical composition in the unit dosage form at a level ranging from about 250-750 mg as measured as the free base form of ATR-101. In more specific embodiments, ATR-101 is present in the solid pharmaceutical composition at a level at or in excess of 50%, 60%, 65% or 70% by weight, as measured as the free base form of ATR-101, of the total weight of the unit dosage form.

In another embodiment, a method is provided for administering a solid pharmaceutical composition, comprising orally administering to a subject in need thereof ATR-101 in unit dosage form.

In a more specific embodiment, such methods comprise oral administration of an acidic agent at or near the time of oral administration of ATR-101 in unit dosage form. Such acidic agents serve to increase gastric acidity (decrease pH) and include, for example, acidic aqueous solutions such as non-diet cola beverages, as well as acidic agents in solid dosage form. In even more specific embodiments, co-administration comprises swallowing or drinking all or a portion of a non-diet cola beverage simultaneously with, or in close proximity to, oral administration of the solid pharmaceutical composition. Representative acidic aqueous solutions have a pH in the range of 2.0 to 3.5, 2.2 to 3.0 or 2.3 to 2.7, inclusive.

In a further embodiment, a kit is provided for co-administration of ATR-101 with an acidic agent. Such kits comprise a plurality of oral unit dosage forms of ATR-101 in combination with an acidic agent for co-administration and/or instructions for co-administration with an acidic agent, at or near the time of oral administration of ATR-101 in unit dosage form.

In an embodiment, a method for treating adrenocortical carcinoma in a patient in need thereof is provided, the method comprising administering to the patient a therapeutically effective amount of the oral dosage product comprising the solid drug form of ATR-101.

In an embodiment, a method for treating congenital adrenal hyperplasia or for treating Cushing's syndrome in a patient in need thereof is provided, the method comprising administering to the patient a therapeutically effective amount of the oral dosage product comprising the solid drug form of ATR-101.

In an embodiment, a method for treating benign adenoma, increased hormone production, adrenocortical carcinoma, congenital adrenal hyperplasia, excess cortisol production, symptoms associated with excess cortisol production, hyperaldosteronism or 21-hydroxylase deficiency in a patient in need thereof is provided, the method comprising administering to the patient a therapeutically effective amount of the oral dosage product comprising the solid drug form of ATR-101.

In an embodiment, a method for reducing adrenocortical tumor size in a patient in need thereof is provided, the method comprising administering to the patient a therapeutically effective amount of the oral dosage product comprising the solid drug form of ATR-101.

In an embodiment, the method further comprises administering a second therapeutic agent. In a more specific embodiment, the second therapeutic agent is a chemotherapeutic agent.

In an embodiment, a method for making ATR-101 in high purity is provided, comprising the step of employing crystalized 2,6-diisopropylanaline hydrochloride salt as an intermediate in the synthesis. In particular, employing 2,6-diisopropylanaline hydrochloride salt in the isocyanate coupling step for the formation of ATR-101 as the free base. This steps allows the large scale production of ATR-101 at high purity levels, minimizing the 2,4-diisopropyl regioisomer and the 2-n-propyl-6-isopropyl isomer impurities. In a further embodiment, formation of the corresponding isocyanate is performed in situ (as opposed to an isolated intermediate) to avoid formation of additional impurities; namely, the symmetrical urea as discussed below. By employing these synthetic steps, ATR-101 can be obtained in high purity at large scale production, such as in excess of 98% (w/w) or 99% (w/w/).

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION

Figure 1:
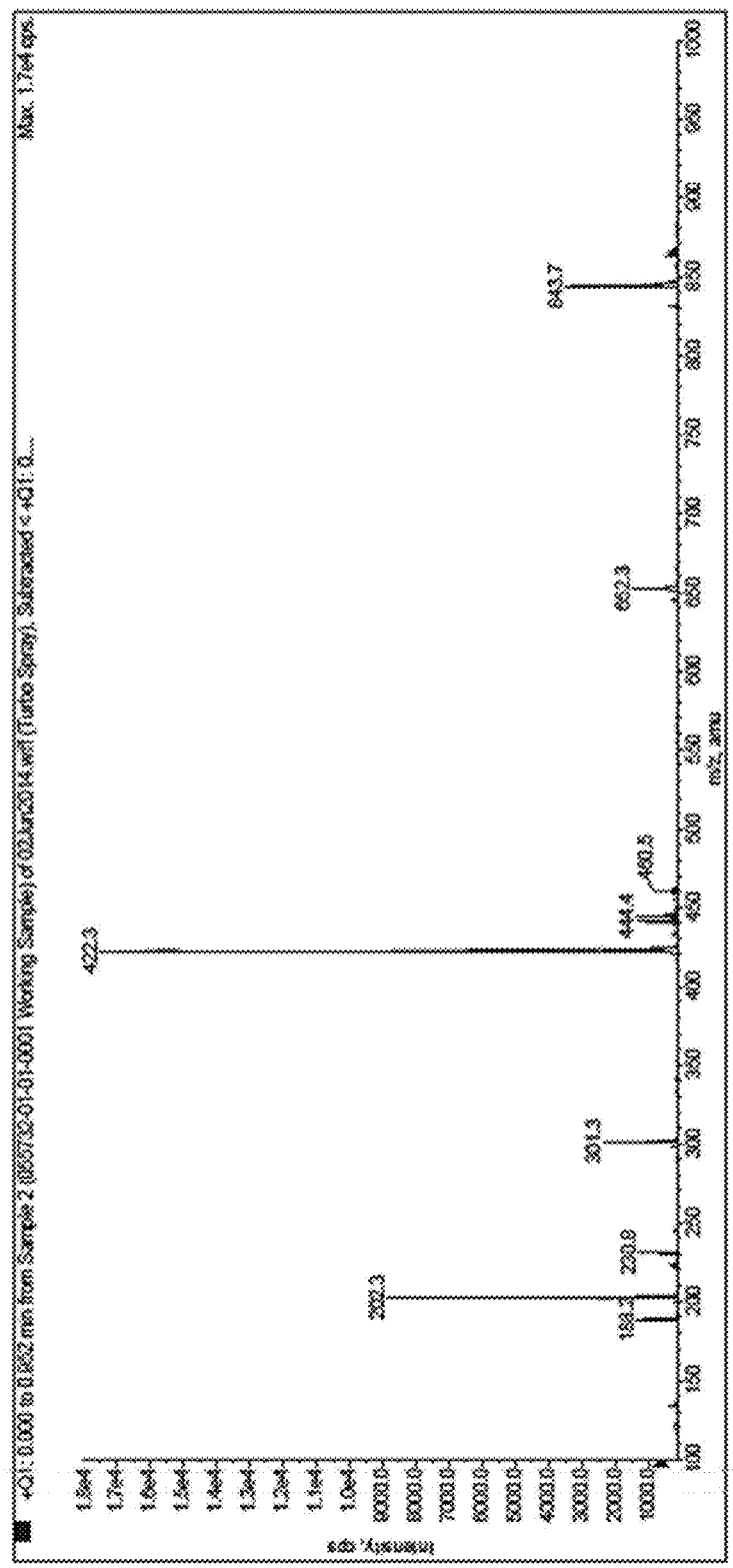
FIG. 1 is the LC/MS Mass spectrum of the solid drug form of ATR-101.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

As used herein, "about" means±20% of the stated value, and includes more specifically values of ±10%, ±5%, ±2% and ±1% of the stated value.

As used herein, "aberrant adrenocortical cellular behavior" includes increased hormone production, Cushing's syndrome, benign adenoma, adrenocortical carcinoma (ACC), metastatic adrenocortical carcinoma, congenital adrenal hyperplasia, hyperaldosteronism including Conn syndrome, a unilateral aldosterone-producing adenoma, bilateral adrenal hyperplasia (or idiopathic hyperaldosteronism (IHA)), renin-responsive adenoma, primary adrenal hyperplasia and glucocorticoid-remediable aldosteronism (GRA), and 21-hydroxylase deficiency.

As used herein, "disorders associated with aberrant adrenocortical cellular behavior" is used herein to mean symptoms and/or conditions that arise, either directly or indirectly, from aberrant adrenocortical cellular behavior. As will become apparent herein, these symptoms and/or conditions that arise, either directly or indirectly, from aberrant adrenocortical cellular behavior are numerous. As used herein, "adrenocortical" and "adrenal cortex" are intended to mean the same.

As used herein, "Cushing's syndrome" means a hormonal disorder caused by prolonged exposure of the body's tissues to high levels of cortisol. Cushing's syndrome is sometimes referred to as "hypercortisolism" (excess cortisol production). Cushing's syndrome includes various subtypes of the disease, including Cushing's disease, adrenal Cushing's syndrome, and ectopic ACTH syndrome, which are categorized by the cause of hypercortisolism. Cushing's disease, also known as pituitary Cushing's, is caused by a pituitary gland tumor which secretes excessive ACTH, which in turn stimulates the adrenal glands to make more cortisol. Ectopic ACTH syndrome is caused by tumors that arise outside the pituitary gland that can produce ACTH, which stimulates cortisol production. Adrenal Cushing's syndrome is caused by an abnormality of the adrenal gland, usually an adrenal tumor, which causes excess cortisol secretion.

As used herein, "subject" means a mammal, including a human.

As used herein, the phrase term "therapeutically effective amount" refers to an amount of a therapeutic agent to treat, ameliorate, or prevent a disease or condition, or to exhibit a detectable therapeutic or preventative effect. The effect is detected by, for example, a reduction in tumor size. The effect is also detected by, for example, chemical markers, steroid levels, or antigen levels. Therapeutic effects also include reduction in physical symptoms, such as decreased body temperature. The precise effective amount for a subject will depend upon the subject's size and health, the nature and extent of the condition, the therapeutics or combination of therapeutics selected for administration, and other variables known to those of skill in the art. The effective amount for a given situation is determined by routine experimentation and is within the judgment of the clinician.

As used herein, "treatment" includes therapeutic applications to slow or stop progression of a disorder, prophylactic application to prevent development of a disorder, and/or reversal of a disorder. Reversal of a disorder differs from a therapeutic application which slows or stops a disorder in that with a method of reversing, not only is progression of a disorder completely stopped, cellular behavior is moved to some degree, toward a normal state that would be observed in the absence of the disorder.

In one embodiment, the disorder is associated with aberrant adrenocortical cellular behavior. Thus, in this context, "treatment" includes therapeutic applications to slow or stop progression of a disorder associated with aberrant adrenocortical cellular behavior, prophylactic application to prevent development of a disorder associated with aberrant adrenocortical cellular behavior, and reversal of a disorder associated with aberrant adrenocortical cellular behavior. In this context, reversal of a disorder differs from a therapeutic application which slows or stops a disorder in that with a method of reversing, not only is progression of a disorder completely stopped, cellular behavior is moved to some degree, toward a normal state that would be observed in the absence of aberrant adrenocortical cellular behavior.

In another embodiment, the disorder is one that would benefit from inhibition of acyl-coenzyme A:cholesterol transferase (ACAT). To this end, ATR-101 is an ACAT1 inhibitor. ACAT is an integral membrane protein localized in the endoplasmic reticulum and catalyzes formation of cholesteryl esters (CE) (also known as cholesterol esters) from cholesterol and fatty acyl coenzyme A. Cholesteryl esters are stored as cytoplasmic lipid droplets in the cell. In mammals, there are two ACAT isoenzymes, ACAT1 and ACAT2. ACAT2 is expressed in the liver and intestine. ACAT1 expression is more ubiquitous and is present in cells and tissues such as macrophages, hepatocytes, enterocytes, renal tubule cells, and neurons, and is highly expressed in the adrenal glands and adrenal cortex.

Altered lipid metabolism has been identified as an important process in cancer. For example, aberrant cholesteryl ester accumulation has been found in advanced prostate cancers, and inhibition of cholesterol esterification has been reported to impair cancer aggressiveness (Yue et al. "Cholesteryl ester accumulation induced by PTEN loss and PI3K/AKT activation underlies human prostate cancer aggressiveness," *Cell Metab.* 4:393-406, 2014). Accordingly, in this embodiment, "treatment" includes therapeutic applications to slow or stop progression of, prophylactic application to prevent development of, or reversal of, a disorder that would benefit from inhibition of ACAT, including disorders that would benefit from inhibition of cholesterol esterification. Representative disorders in this regard include cancers in which aberrant cholesteryl ester accumulation are present, and/or in which cholesterol esterification impairs cancer growth or aggressiveness. Representative cancers in this regards include (but are not limited to) prostate cancer and ovarian cancer.

A solid drug form of ATR-101, particularly in the context of a solid powder suitable for capsule or tablet formulation, has proved difficult with existing forms of the drug product. For example, deficiencies in existing drug product include lack of flowability and a bulk density ill-suited for capsule or tablet formulation.

ATR-101 of the solid pharmaceutical composition may be characterized by the median diameter of its particles, as determined in dry-dispersion mode using a Malvern Mastersizer 2000 equipped with a Scirocco 2000 module (measuring range 0.02 to 2000 µm). For example, the "d(0.5)" particle size distribution is the median diameter of the particle size distribution, and represents the particle size at which 50% of the particles are larger and 50% of the particles are smaller than the d(0.5) value. Similarly, the "d(0.1)" value is the particle size at which 10% of the particles are smaller and 90% of the particles are larger, and the "d(0.9)" value is the particle size at which 90% of the particles are smaller and 10% of the particles are larger.

In one embodiment, ATR-101 of the solid pharmaceutical composition has a d(0.5) particle size distribution of about 12 μm, and can be further characterized as having a d(0.1) particle size distribution of about 2 μm, and/or as having a d(0.9) particle size distribution of about 49 μm. In other embodiments, ATR-101 of the solid pharmaceutical composition has a d(0.5) particle size distribution ranging from 5 to 20 μm, from 6 to 18 μm, from 8 to 16 μm, from 10 to 14 μm, or from 2 to 10 μm. In still other embodiments, ATR-101 of the solid pharmaceutical composition has a d(0.1) particle size distribution greater than 1 μm and/or a d(0.9) particle size distribution less than 60 μm or, in another embodiment, less than 50 μm.

In other embodiments, the solid drug form has a d(0.5) particle size distribution ranging from 5 to 20 μm, from 6 to 18 μm, from 8 to 16 μm, or from 10 to 14 μm. In still other embodiments, the solid drug form has a d(0.1) particle size distribution greater than 1 μm and/or a d(0.9) particle size distribution less than 60 μm.

In other embodiments, a solid drug form of ATR-101 is provided having a differential scanning calorimetry (DSC) onset at about 228.28° C. and endotherm at about 230.93° C. In other embodiments, a solid drug form of ATR-101 is provided having a differential scanning calorimetry (DSC) onset at about 228-229° C. and endotherm at about 231-232° C.

In still other embodiments, a solid drug form of ATR-101 is provided having a purity in excess of 98% (w/w). In other embodiments, ATR-101 is provided having a purity in excess of 98.5% (w/w) or 99% (w/w).

The solid drug form of ATR-101 may be ground, milled and/or sieved, provided that the particle size distribution of the resulting product remains within the ranges noted above. Such additional grinding or milling may be employed to provide a more uniform particle size distribution. Procedures for the same are known by those skilled in the field of milling/grinding of solid drug materials.

The solid pharmaceutical composition may be in a variety of forms suitable for oral administration, such as a capsule, pill, granule, suspension, pellet, tablet or powder, and contains one or more pharmaceutically acceptable carriers or excipients. In a specific embodiment, the solid pharmaceutical composition is in the form of a compressed tablet, which may be coated, for example with a nonfunctional film or a release-modifying coating. Pharmaceutically acceptable carriers and excipients are well known in the art, such as those disclosed in Remington: The Science and Practice of Pharmacy, 22$^{nd}$ Edition, Allen, Lloyd V., Jr. Ed. (2012) (incorporated herein by reference), and include (without limitation) diluents, binding agents, adhesives, disintegrants, wetting agents, lubricant, anti-adherent, glidant, tonicity agent and/or surfactant.

In one embodiment, the solid drug form of ATR-101 is not formulated with any additional components. In this context, a suitable solid form includes a powder. When ATR-101 is in capsule form, the capsule may solely contain the solid drug form, such as ATR-101 in powder form, without the presence of any fillers or carriers. In this embodiment, the capsule may contain, for example, from 25 to 1000 mg, such as 25 mg, 50 mg, 100 mg, 125 mg, 200 mg, 300 mg, 400 mg, 500 mg, 600 mg, 700 mg, 750 mg or 1000 mg, of the solid drug form of ATR-101 (as measured as the free base).

In another embodiment, the solid drug form of ATR-101 may be formulated as a pharmaceutical composition comprising, in addition to the solid drug form of ATR-101, one or more additional pharmaceutically acceptable components as described in Remington's Pharmaceutical Sciences 16th edition, Osol, A., Ed. (1980). Pharmaceutically acceptable carrier and/or diluents are familiar to those skilled in the art, and generally do not adversely affect the desired characteristics of the composition.

In various aspects, the solid pharmaceutical composition includes a diluent, either individually or in combination, such as, and without limitation, lactose, including anhydrous lactose and lactose monohydrate; lactitol; maltitol; mannitol; sorbitol; xylitol; dextrose and dextrose monohydrate; fructose; sucrose and sucrose-based diluents such as compressible sugar, confectioner's sugar and sugar spheres; maltose; inositol; hydrolyzed cereal solids; starches (e.g., corn starch, wheat starch, rice starch, potato starch, tapioca starch, etc.), starch components such as amylose and dextrates, and modified or processed starches such as pregelatinized starch; dextrins; celluloses including powdered cellulose, microcrystalline cellulose, silicified microcrystalline cellulose, food grade sources of α- and amorphous cellulose and powdered cellulose, and cellulose acetate; calcium salts including calcium carbonate, tribasic calcium phosphate, dibasic calcium phosphate dihydrate, monobasic calcium sulfate monohydrate, calcium sulfate and granular calcium lactate trihydrate; magnesium carbonate; magnesium oxide; bentonite; kaolin; sodium chloride; and the like. The diluent or diluents selected should exhibit suitable flow properties and, where tablets are desired, compressibility.

In various aspects, the solid pharmaceutical composition includes binding agents or adhesives which are useful excipients, particularly where the composition is in the form of a tablet. Such binding agents and adhesives should impart sufficient cohesion to the blend being formulated in a tablet to allow for normal processing operations such as sizing, lubrication, compression and packaging, but still allow the tablet to disintegrate and the compound to be absorbed upon ingestion. Suitable binding agents and adhesives include, either individually or in combination, acacia; tragacanth; glucose; polydextrose; starch including pregelatinized starch; gelatin; modified celluloses including methylcellulose, carmellose sodium, hydroxypropylmethylcellulose (HPMC or hypromellose), hydroxypropyl-cellulose, hydroxyethylcellulose and ethylcellulose; dextrins including maltodextrin; zein; alginic acid and salts of alginic acid, for example sodium alginate; magnesium aluminum silicate; bentonite; polyethylene glycol (PEG); polyethylene oxide; guar gum; polysaccharide acids; polyvinylpyrrolidone (povidone), for example povidone K-15, K-30 and K-29/32; polyacrylic acids (carbomers); polymethacrylates; and the like. One or more binding agents and/or adhesives, if present, constitute in various aspects, in total about 0.5% to about 25%, for example about 0.75% to about 15%, or about 1% to about 10%, by weight of the composition.

In various aspects, the solid pharmaceutical composition includes a disintegrant. Suitable disintegrants include, either individually or in combination, starches including pregelatinized starch and sodium starch glycolate; clays; magnesium aluminum silicate; cellulose-based disintegrants such as powdered cellulose, microcrystalline cellulose, methylcellulose, low-substituted hydroxypropylcellulose, carmellose, carmellose calcium, carmellose sodium and croscarmellose sodium; alginates; povidone; crospovidone; polacrilin potassium; gums such as agar, guar, locust bean, karaya, pectin and tragacanth gums; colloidal silicon dioxide; and the like. One or more disintegrants, if present, typically constitute in total about 0.2% to about 30%, for example about 0.2% to about 10%, or about 0.2% to about 5%, by weight of the composition.

In various aspects, the solid pharmaceutical composition includes a wetting agent. Wetting agents, if present, are normally selected to maintain the compound in close association with water, a condition that is believed to improve bioavailability of the composition. Non-limiting examples of surfactants that can be used as wetting agents include, either individually or in combination, quaternary ammonium compounds, for example benzalkonium chloride, benzethonium chloride and cetylpyridinium chloride; dioctyl sodium sulfosuccinate; polyoxyethylene alkylphenyl ethers, for example nonoxynol 9, nonoxynol 10 and octoxynol 9; poloxamers (polyoxyethylene and polyoxypropylene block copolymers); polyoxyethylene fatty acid glycerides and oils, for example polyoxyethylene (8) caprylic/capric mono- and diglycerides, polyoxyethylene (35) castor oil and polyoxyethylene (40) hydrogenated castor oil; polyoxyethylene alkyl ethers, for example ceteth-10, laureth-4, laureth-23, oleth-2, oleth-10, oleth-20, steareth-2, steareth-10, steareth-20, steareth-100 and polyoxyethylene (20) cetostearyl ether; polyoxyethylene fatty acid esters, for example polyoxyethylene (20) stearate, polyoxyethylene (40) stearate and polyoxyethylene (100) stearate; sorbitan esters; polyoxyethylene sorbitan esters, for example polysorbate 20 and polysorbate 80; propylene glycol fatty acid esters, for example propylene glycol laureate; sodium lauryl sulfate; fatty acids and salts thereof, for example oleic acid, sodium oleate and triethanolamine oleate; glyceryl fatty acid esters, for example glyceryl monooleate, glyceryl monostearate and glyceryl palmitostearate; sorbitan esters, for example sorbitan monolaurate, sorbitan monooleate, sorbitan monopalmitate and sorbitan monostearate; tyloxapol; and the like. One or more wetting agents, if present, typically constitute in total about 0.25% to about 15%, preferably about 0.4% to about 10%, and more preferably about 0.5% to about 5%, by weight of the composition.

In various aspects, the solid pharmaceutical composition includes a lubricant. Lubricants reduce friction between a tableting mixture and tableting equipment during compression of tablet formulations. Suitable lubricants include, either individually or in combination, glyceryl behenate; stearic acid and salts thereof, including magnesium, calcium and sodium stearates; hydrogenated vegetable oils; glyceryl palmitostearate; talc; waxes; sodium benzoate; sodium acetate; sodium fumarate; sodium stearyl fumarate; PEGs (e.g., PEG 4000 and PEG 6000); poloxamers; polyvinyl alcohol; sodium oleate; sodium lauryl sulfate; magnesium lauryl sulfate; and the like. One or more lubricants, if present, typically constitute in total about 0.05% to about 10%, for example about 0.1% to about 8%, or about 0.2% to about 5%, by weight of the composition. Magnesium stearate is a particularly useful lubricant.

In various aspects, the solid pharmaceutical composition includes an anti-adherent. Anti-adherents reduce sticking of a tablet formulation to equipment surfaces. Suitable anti-adherents include, either individually or in combination, talc, colloidal silicon dioxide, starch, DL-leucine, sodium lauryl sulfate and metallic stearates. One or more anti-adherents, if present, typically constitute in total about 0.1% to about 10%, for example about 0.1% to about 5%, or about 0.1% to about 2%, by weight of the composition.

In various aspects, the solid pharmaceutical composition includes a glidant. Glidants improve flow properties and reduce static in a tableting mixture. Suitable glidants include, either individually or in combination, colloidal silicon dioxide, starch, powdered cellulose, sodium lauryl sulfate, magnesium trisilicate and metallic stearates. One or more glidants, if present, typically constitute in total about 0.1% to about 10%, for example about 0.1% to about 5%, or about 0.1% to about 2%, by weight of the composition.

In various aspects, the solid pharmaceutical composition includes a surfactant. A surfactant may also be added to reduce aggregation of the compound and/or to minimize the formation of particulates in the formulation and/or to reduce adsorption. Exemplary surfactants include nonionic surfactants such as polysorbates (e.g., polysorbate 20 or polysorbate 80) or poloxamers (e.g., poloxamer 188). Exemplary concentrations of surfactant may range from about 0.001% to about 0.5%, or from about 0.005% to about 0.2%, or alternatively from about 0.004% to about 0.01% w/v.

In various aspects, the solid pharmaceutical composition may also include various materials that modify the physical form of the dosage unit. For example, the composition may include materials that form a coating shell around the active ingredients. The materials that form the coating shell are typically inert, and may be selected from, for example, sugar, shellac, polymers, plasticizers, pigments, or other coating agents.

In various aspects, the solid pharmaceutical composition is in the form of a solid powder and is encased within a suitable capsule, such as a gelatin capsule. The amount of drug contained within such a capsule can vary depending upon recognized factors, such as frequency and duration of therapy, dose intervals, excretion rate, the recipient's age, body weight, sex, diet, medical history and general state (e.g., health), the severity of the disease, and/or the size, malignancy and invasiveness of a tumor to be treated The compound is thus in a form suitable, and administered at a dosage sufficient to achieve a desired therapeutic or prophylactic effect.

Administration of the solid dosage form of ATR-101 is typically in the form of one or more dosage units wherein, for example, a single tablet or capsule is a single dosage unit. The dosage amount and frequency are selected to create a therapeutically effective level of the agent. For example, frequency may be daily; two, three, or four times daily; alternating days; every third day; or 2, 3, 4, 5, or 6 times per week; weekly; twice a month; monthly or more or less frequently, as necessary, depending on the response or condition and the recipient tolerance of the therapy. Maintenance dosages over a longer period of time, such as 4, 5, 6, 7, 8, 10 or 12 weeks or longer, are contemplated, and dosages may be adjusted as necessary. Similarly, intermittent dosing, where dosing is stopped for a period of time and then restarted, is also contemplated. The progress of the therapy may be monitored by conventional techniques and assays, such as by monitoring tumor size and/or cortisol levels, and is within the skill in the art.

In one embodiment, oral administration of a plurality of dosage units is contemplated once daily, twice daily, three times daily or four times daily. Depending on the amount of ATR-101 contained within, for example, a single tablet, a plurality of unit dosage forms may range from 2 to 30 tablets administered once daily, twice daily, three times daily or four times daily. In one embodiment, and depending upon exposure as discussed below, administration may be 4-24 tablets twice daily, or 6-12 tablets twice daily.

In some embodiments, the solid drug form is administered at a dosage, on a daily basis, of from about 0.1 mg/kg to about 200 mg/kg. Suitable dosages include, but are not limited to, from 0.5 mg/kg to 150 mg/kg, from 0.75 mg/kg to 100 mg/kg, from 1 mg/kg to 50 mg/kg, from 2 mg/kg to 40 and from 3 mg/kg to 35 mg/kg. Suitable dosages also include from 1 mg/kg to 5 mg/kg and from 2 mg/kg to 4 mg/kg, as well as from 10 mg/kg to 50 mg/kg and from 20 mg/kg to 40 mg/kg.

In more specific embodiments, ATR-101 is present in the solid pharmaceutical composition at a level at or in excess of 50% by weight, as measured as the free base form of ATR-101, of the total weight of the unit dosage form. In a further embodiment, ATR-101 is present in the solid pharmaceutical composition at a level at or in excess of 60% by weight, as measured as the free base form of ATR-101, of the total weight of the unit dosage form. In a further embodiment, ATR-101 is present in the solid pharmaceutical composition at a level at or in excess of 65% by weight, as measured as the free base form of ATR-101, of the total weight of the unit dosage form. In still a further embodiment, ATR-101 is present in the solid pharmaceutical composition at a level at or in excess of 70% by weight, as measured as the free base form of ATR-101, of the total weight of the unit dosage form. Surprisingly, the nature of ATR-101 itself, including particle size distribution, bulk density, compressibility and the like, allows for such elevated drug levels within the solid pharmaceutical composition.

In one embodiment, the solid pharmaceutical composition may be co-administered with an acidic agent to increase exposure of ATR-101 upon oral administration. In some embodiments, the co-administered agent is an acidic aqueous solution to increase exposure of ATR-101 upon oral administration. In other embodiments, the acidic agent is in solid dosage form, for example a solid dosage form of an acid such as citric acid.

Accordingly, in one embodiment a method is provided for co-administration of the solid pharmaceutical composition in combination with an acidic aqueous solution. Such acidic aqueous solutions serve to increase gastric acidity (decrease pH) and thereby increase exposure of ATR-101 upon oral administration. In more specific embodiments, co-administration comprises swallowing or drinking the acidic aqueous solution simultaneously with, or in close proximity to, oral administration of the solid pharmaceutical composition. For example, the subject may use the acidic aqueous solution as an aid to swallow one or more tablets containing ATR-101, such as by drinking the acidic aqueous solution prior to, simultaneously with, or following shortly after swallowing such tablets.

The acidic aqueous solution enhances exposure of ATR-101 by increasing gastric acidity (lowering pH) or maintaining gastric acidity, and thereby aiding in absorption of ATR-101 into the subject's blood stream. To this end, representative acidic aqueous solutions have a pH in the range of 2.0 to 3.5, 2.2 to 3.0 or 2.3 to 2.7, inclusive. In one embodiment, the acidic aqueous solution is a non-diet cola beverage, such as Coca-Cola®, PepsiCola® or the like. The amount of the acidic aqueous solution co-administration with the solid pharmaceutical composition should be sufficient to increase or maintain gastric acidity at a level such that increased exposure of ATR-101 is achieved upon oral administration. For example, co-administration can include a single sip or swallow, which is typically about 0.5 ounces of liquid, or can include multiple sips or swallows depending, for example, on the number of unit dosages (e.g., tablets) that are being swallowed at a given time. Thus, the amount of acidic aqueous solution that is co-administered typically ranges from a single sip (0.5 ounces) to 24 sips, which would correspond to a 12 ounce can of a non-diet cola beverage.

Methods of the present invention include treatment of a disorder by administrating to a subject in need thereof a therapeutically effective amount of the solid pharmaceutical composition comprising ATR-101. In various embodiments, the methods comprise co-administration to a subject in need thereof a therapeutically effective amount of the solid pharmaceutical composition in combination with an acidic agent, such as an acidic aqueous solution or acidic solid dosage form. In various aspects, methods are also provided for slowing or stopping progression of disorder, preventing a disorder, or reversing a disorder.

In one embodiment, the disorder is a disorder associated with aberrant adrenocortical cellular activity, and the method comprises administration to a subject in need thereof a therapeutically effective amount of the solid pharmaceutical composition. In various aspects, methods are also provided for slowing or stopping progression of a disorder associated with aberrant adrenocortical cellular activity. In various aspects, methods are also provided for preventing a disorder associated with aberrant adrenocortical cellular activity. In various aspects, methods are also provided for reversing a disorder associated with aberrant adrenocortical cellular activity.

In this embodiment, methods according to the present invention include treating: increased hormone production, benign adenoma, adrenocortical carcinoma (ACC), metastatic adrenocortical carcinoma, congenital adrenal hyperplasia, Cushing's syndrome, excess cortisol production, symptoms associated with excess cortisol production, hyperaldosteronism, Conn syndrome, unilateral aldosterone-producing adenoma, bilateral adrenal hyperplasia (or idiopathic hyperaldosteronism (IHA)), primary adrenal hyperplasia, glucocorticoid-remediable aldosteronism (GRA) and/or 21-hydroxylase deficiency. Such methods involve administration to a subject in need thereof a therapeutically effective amount of the solid pharmaceutical composition.

In other embodiments, methods according to the present invention include reducing adrenocortical tumor size, and/or inhibiting aberrant adrenal hormone production in a patient, by administration to a subject in need thereof a therapeutically effective amount of the solid pharmaceutical composition.

Methods according to the present invention also include slowing or stopping progression of: increased hormone production, benign adenoma, adrenocortical carcinoma, metastatic adrenocortical carcinoma, Cushing's syndrome, excess cortisol production, symptoms associated with excess cortisol production, congenital adrenal hyperplasia, hyperaldosteronism, Conn syndrome, unilateral aldosterone-producing adenoma, bilateral adrenal hyperplasia (or idiopathic hyperaldosteronism (IHA)), renin-responsive adenoma, primary adrenal hyperplasia, glucocorticoid-remediable aldosteronism (GRA), 21-hydroxylase deficiency. Such methods involve administration to a subject in need thereof a therapeutically effective amount of the solid pharmaceutical composition.

In another embodiment, the disorder is a disorder that would benefit from inhibition of ACAT, and the method comprises administration to a subject in need thereof a therapeutically effective amount of the solid pharmaceutical composition. In various aspects, methods are also provided for slowing or stopping progression of a disorder that would benefit from inhibition of ACAT. In various aspects, methods are also provided for preventing a disorder that would benefit from inhibition of ACAT. In various aspects, methods are also provided for reversing a disorder that would benefit from inhibition of ACAT. In this embodiment, methods according to the present invention include treating prostate cancer and ovarian cancer.

Methods according to the present invention also include co-therapy by administration of a second therapeutic agent, including known chemotherapeutics, targeting agents, adrenalysis agents, metformin, everolimus, and/or IGF1R antagonist. In one embodiment, co-administration further comprises administering mitotane. Examples of suitable chemotherapeutic and radio therapeutic agents include, but are not limited to: an anti-metabolite; a DNA-damaging agent; a cytokine useful as a chemotherapeutic agent; a covalent DNA-binding drug; a topoisomerase inhibitor; an anti-mitotic agent; an anti-tumor antibiotic; a differentiation agent; an alkylating agent; a methylating agent; a hormone or hormone antagonist; a nitrogen mustard; a radio sensitizer; a photosensitizer; a radiation source, optionally together with a radio sensitizer or photosensitizer; or other commonly used therapeutic agents.

In another embodiment, kits are provided for co-administration of ATR-101 with an acidic agent to increase exposure of ATR-101 upon oral administration. Such kits comprise a plurality of oral unit dosage forms of ATR-101 in combination with an acidic agent for co-administration. Alternatively, such kits comprise a plurality of oral unit dosage forms of ATR-101 in combination with instructions for co-administration with an acidic agent.

In further embodiments, methods are provided for producing ATR-101 at high purity, particularly in the context of large-scale manufacturing. As set forth in more detail in Example 5, a method for making ATR-101 in high purity is provided, comprising the step of employing crystalized 2,6-diisopropylanaline hydrochloride salt as an intermediate in the synthesis.

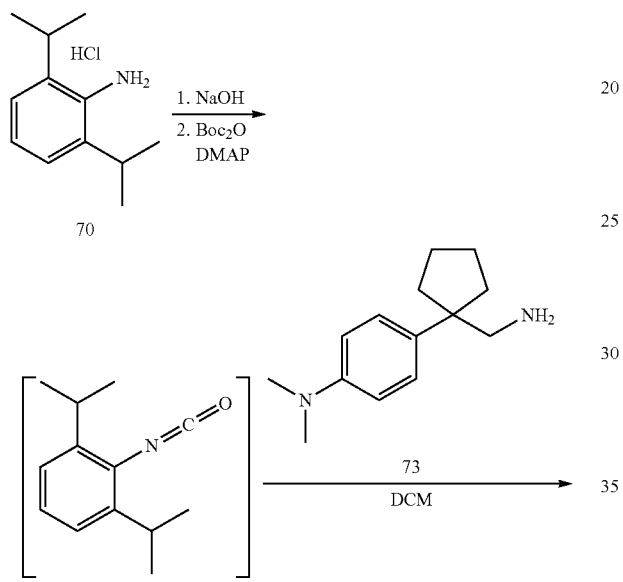

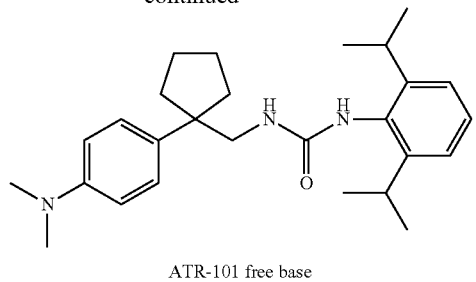

ATR-101 free base

In particular, the method employs 2,6-diisopropylanaline hydrochloride salt 70 in the isocyanate coupling step (depicted above) for the formation of ATR-101 as the free base. This steps allows the large scale production of ATR-101 at high purity levels, minimizing the 2,4-diisopropyl regioisomer and the 2-n-propyl-6-isopropyl isomer impurities. In a futher embodiment, formation of the corresponding isocyanate is performed in situ (as opposed to an isolated intermediate) to avoid formation of additional impurities; namely, the symmetrical urea as discussed below. By employing these synthetic steps, ATR-101 can be obtained in high purity at large scale production, such as in excess of 98% (w/w) or 98.5% (w/w) or 99% (w/w/).

Various alternative embodiments and examples of the invention are described herein. These embodiments and examples are illustrative and should not be construed as limiting the scope of the invention.

EXAMPLES

Example 1

Synthesis of Solid Drug Form of ATR-101

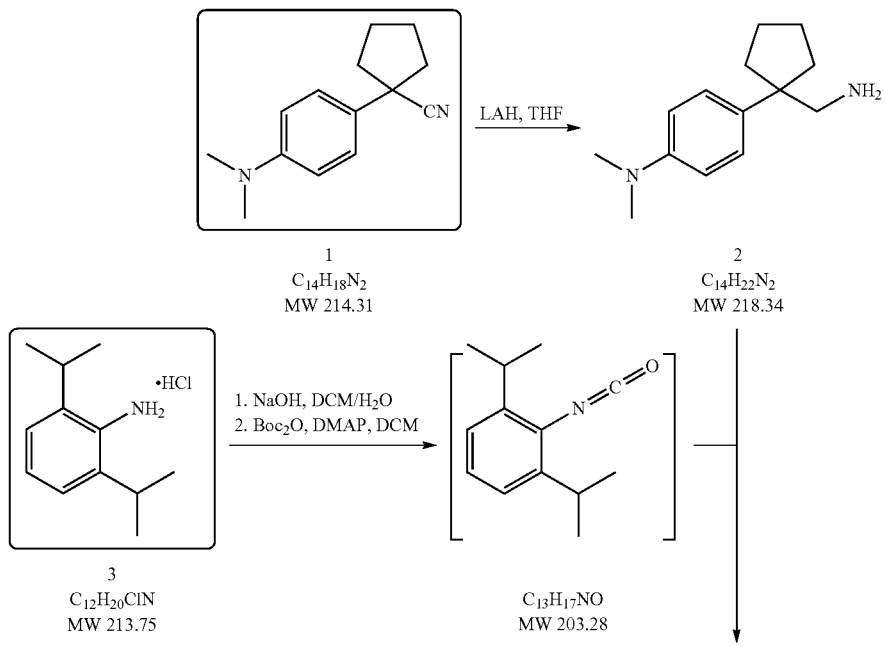

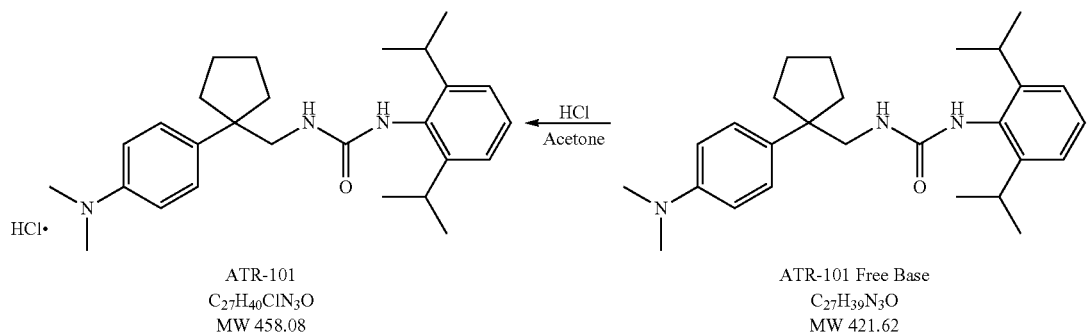

ATR-101
$C_{27}H_{40}ClN_3O$
MW 458.08

ATR-101 Free Base
$C_{27}H_{39}N_3O$
MW 421.62

Step 1: Preparation of Primary Amine 2 from the Nitrile 1

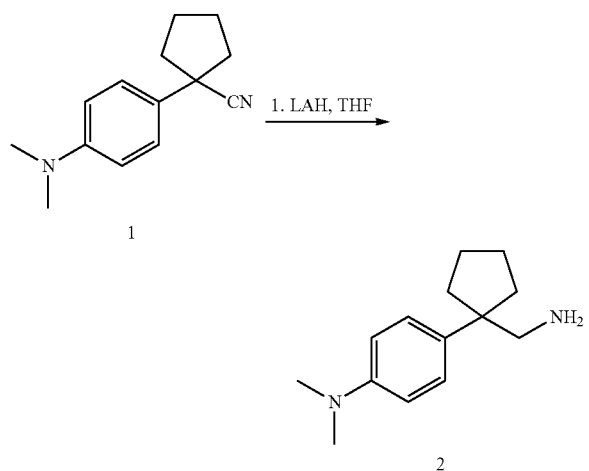

Tetrahyrofuran (THF) and Compound 1 are charged to a reactor vessel and a lithium aluminum hydride (LAH) solution in THF is added slowly. After the addition, the reaction mixture is warmed to 45° C. and stirred until in-process HPLC analysis indicates that the reaction is complete. The reaction mixture is cooled to between 0 and 10° C. and aqueous NaOH is added slowly while controlling the temperature to between 0 and 10° C. The mixture is then warmed to between 20 and 25° C. and any inorganic salts removed by filtration. The solids are then washed with additional THF.

The filtrate is distilled under vacuum. Acetonitrile (MeCN) is added and the distillation continued to reduce the total volume. $H_2O$ is added and the solution is cooled to 20° C., and seeded if necessary. Additional water is added to the slurry and cooled to between 0 and 5° C. and filtered. The crystallization vessel and filter cake is washed with MeCN and water (1:2 mixture) and dried under vacuum between 40 to 45° C. to produce Compound 2. Typical yield: 85%.

Step 2: Preparation of ATR-101 Free Base

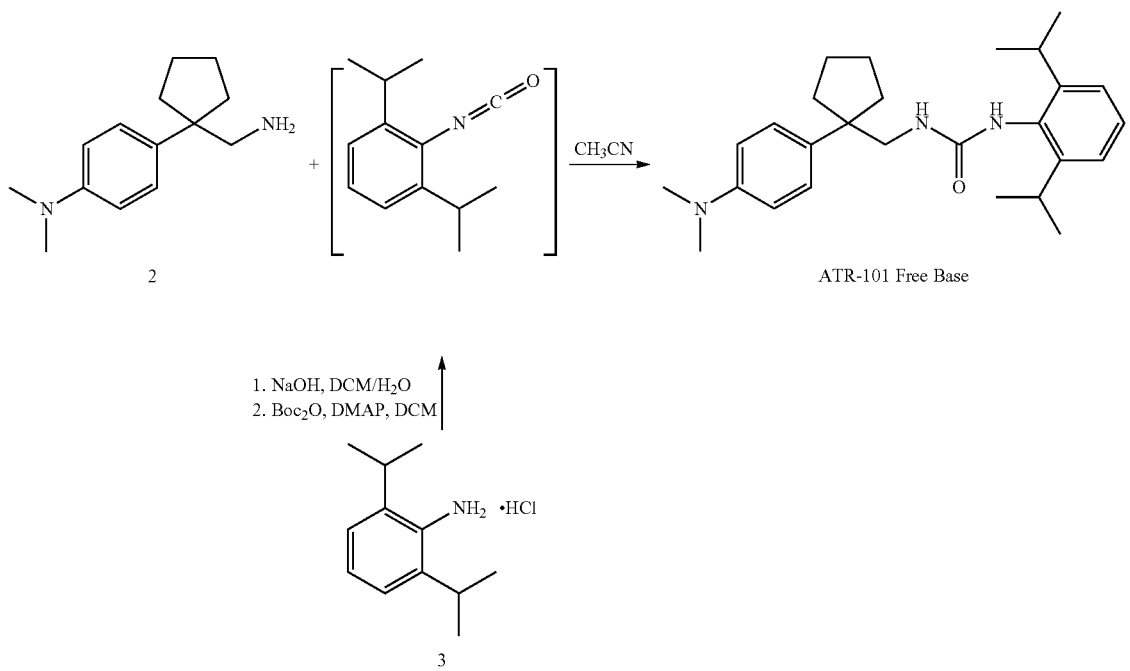

2,6-Diisopropyl aniline hydrochloride (Compound 3) is converted to the corresponding free base by stirring in a mixture of dichloromethane (DCM) and 10% aqueous NaOH. The organic phase is separated and washed with water. The DCM solution containing the aniline free base is concentrated by distillation.

4-dimethylaminopyridine (DMAP) and DCM are charged to a separate reaction vessel. The mixture is cooled and a solution of di-tert-butyl dicarbonate ($Boc_2O$) in DCM is slowly added while the temperature is maintained between 0 and 5° C. The aniline free base solution is then slowly added to the reaction vessel. A complete conversion of aniline to the isocyanate is verified by in-process HPLC analysis.

Compound 2 and MeCN are charged to a separate vessel and this solution is cooled to between 0 and 5° C. The isocyanate intermediate solution (prepared above) is slowly added while the temperature is maintained between 0 and 5° C., and stirred until in-process HPLC indicates that the reaction is complete.

The reaction mixture is distilled under vacuum, and isopropyl alcohol (IPA) is added and the distillation is continued. The resulting solution is cooled and seeded, if necessary. After crystallization occurs, water is added and the mixture is cooled to between 0 and 5° C., and filtered. The crystallization vessel and filter cake is washed with isopropanol:water (1:1) and the product cake is dried under vacuum to yield ATR-101 as the free base. Typical yield: 89%

Step 3: Preparation of Solid Drug Form of ATR-101

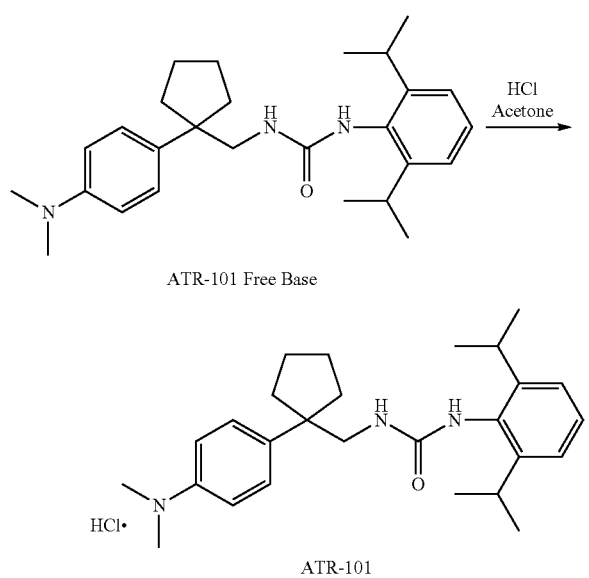

The ATR-101 free base is dissolved in acetone and filtered to remove particulates. Additional acetone is used to rinse the dissolution vessel and filter. Concentrated hydrochloric acid (HCl) is added while maintaining the reaction at room temperature. The resultant slurry is filtered and the cake is washed with acetone. The resulting solid is dried under vacuum between 40 and 45° C. to obtain the solid drug form of ATR-101. Typical yield: 70-80%.

Example 2

Characterization of the Solid Drug Form of ATR-101

The solid drug form of ATR-101 was analyzed to fully characterize the material and provide proof of structure.

Elemental Analysis

An elemental (CHN) analysis was conducted, in duplicate, of the solid drug form of ATR-101. The results are summarized in Table 1 and are in agreement with the theoretical values calculated for the molecular ATR-101 drug substance formula of $C_{27}H_{39}N_3O$ HCl.

TABLE 1

| Element | Theoretical Values | Experimental Results |
| --- | --- | --- |
| % C | 70.79 | 70.63 |
| % H | 8.80 | 8.44 |
| % N | 9.17 | 9.14 |
| % O | 3.50 | 3.56 |
| % Cl | 7.74 | 7.84 |

Chloride Content

The solid drug form of ATR-101 is prepared as its HCl salt. To confirm the chloride content (and the stoichiometry), the hydrochloride salt was analyzed by Ion Chromatography using a validated method. The w/w % result showed 7.8% chloride present. The theoretical value for a mono hydrochloride salt is 7.7%. The experimental result conforms to the theoretical value for the mono-hydrochloride salt.

Mass Spectrometry

Mass spectrometry studies were conducted in accordance with USP<736> using an AB Sciex API 2000 LC/MS/MS system. The samples were analyzed by electrospray ionization in positive mode. The base peak observed was 422.3 (M+H—HCl), consistent with the parent compound (see FIG. 1). Two minor peaks were observed, at 301.3 and 202.3 (uncharacterized fragments). The combined data of the LC/MS and CHN results support the molecular formula assignment of $C_{27}H_{39}N_3O$ and mass of 421.63 g/mol for the free base and $C_{27}H_{39}N_3O$. HCl (mass of 458.09 g/mol) for the mono hydrochloride salt.

Nuclear Magnetic Resonance (NMR)—$^1$H NMR

Figure 2:
FIG. 2 is the proton NMR spectrum of the solid drug form of ATR-101.

The proton NMR spectrum of the solid drug form of ATR-101 was obtained using a Varian Gemini 400 MHz spectrometer and. The sample was dissolved in $CD_3OD$. The resulting proton NMR spectrum is shown in FIG. 2.

Two-Dimensional (2D) NMR

Figure 3:
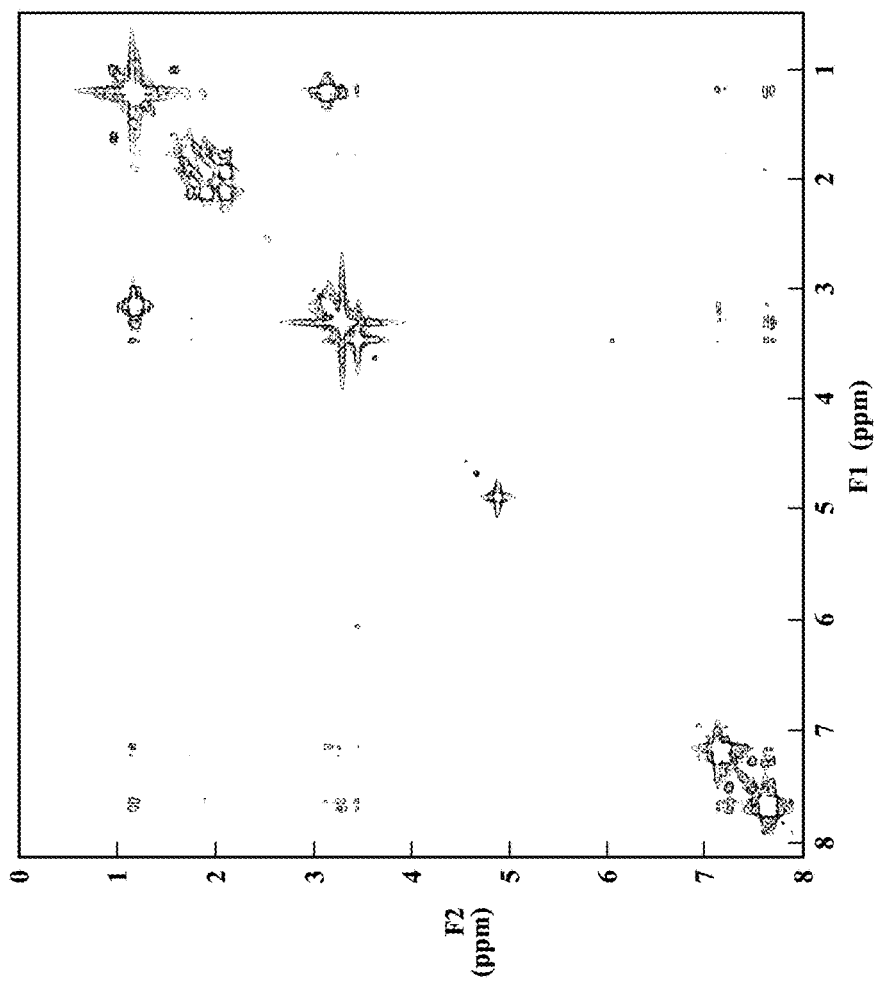
FIG. 3 is the 2-D $^1$H-NMR spectrum (COSY) of the solid drug form of ATR-101.

The 2D proton NMR spectrum (COSY) shown in FIG. 3 confirmed some of the connectivity expected for the solid drug form of ATR-101. In particular the resonance at 1.2 ppm is strongly correlated to the resonance at 3.1. This correlation together with the splitting pattern observed for the peak at 3.1 strongly suggests an isopropyl moiety. Further, the data from these spectra show a strong correlation between each of the broad peaks at 1.6-2.2 ppm, consistent with a cycloalkyl functionality in which no heteroatoms or other non-alkyl substitution is present.

Carbon 13 NMR ($^{13}$C NMR)

Figure 4:
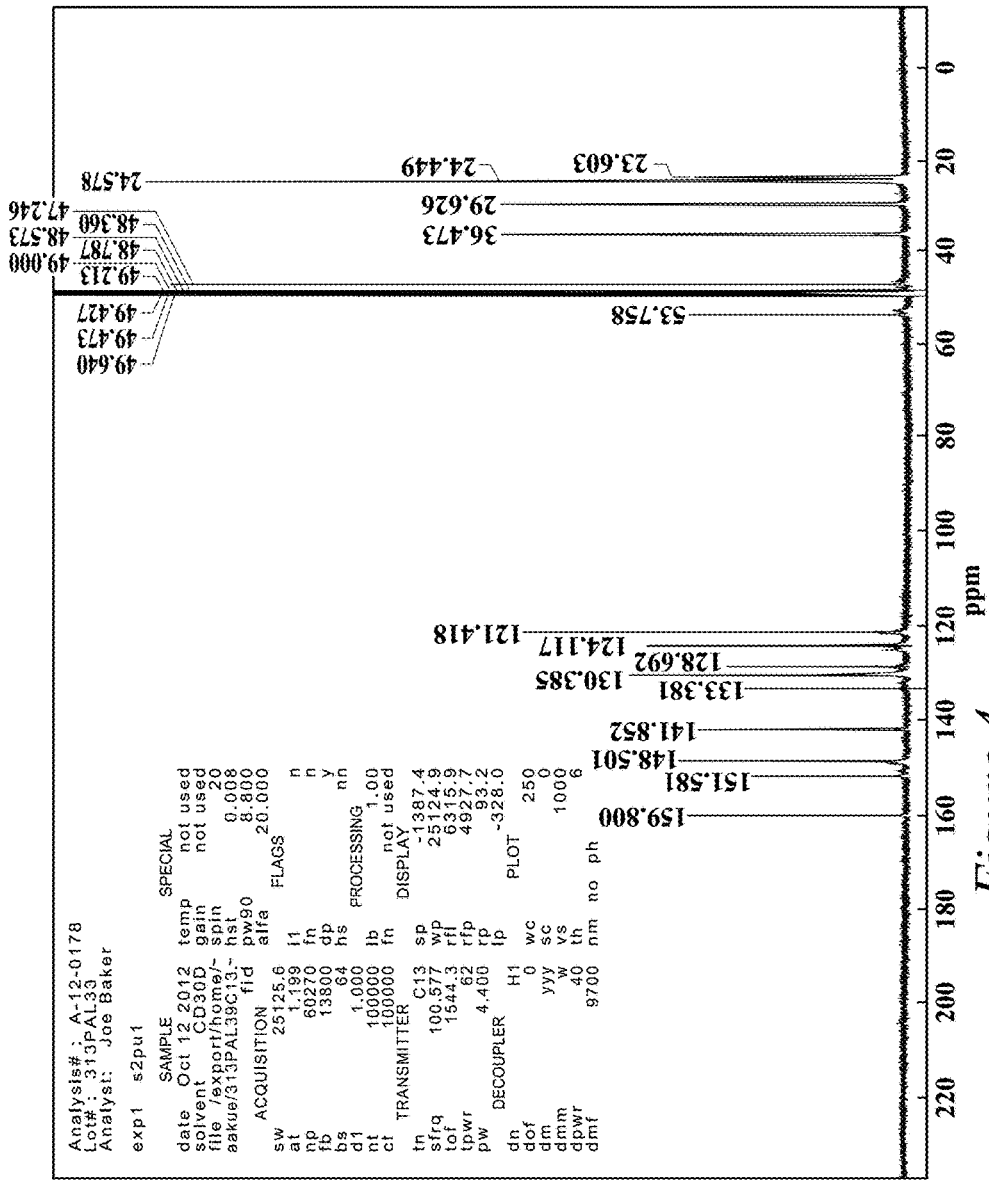
FIG. 4 is the $^{13}$C NMR spectrum of the solid drug form of ATR-101.

The 100 MHz $^{13}$C NMR spectrum of the solid drug form of ATR-101 was obtained using a Varian Gemini 400 MHz spectrometer. The sample was dissolved in $CD_3OD$. The resulting $^{13}$C NMR spectrum is shown in FIG. 4. The numbering of the carbon atoms for the analysis of the spectrum is shown below, and the interpretation is shown in Table 2. The observed signals are consistent with the structure of ATR-101.

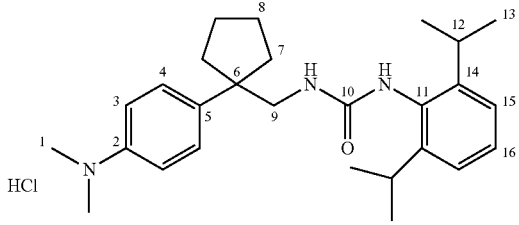 [SMILES: Cl ; CC(C)c1cccc(C(C)C)c1NC(=O)NCC1(c2ccc(N(C)C)cc2)CCCC1]

TABLE 2

| Shift (ppm) | Prediction (ppm) | # of Carbons | Assignment |
|---|---|---|---|
| 159.8 | 155.0 | 1 | C10 |
| 151.6 | 146.1 | 2 | C14 |
| 148.5 | 145.7 | 1 | C5 |
| 141.9 | 143.1 | 1 | C2 |
| 133.4 | 138.3 | 1 | C11 |
| 130.4 | 128.9 | 2 | C4 |
| 128.7 | 128.0 | 1 | C16 |
| 124.1 | 124.6 | 2 | C3 |
| 121.4 | 123.3 | 2 | C15 |
| 53.8 | 54.5 | 1 | C9 |
| 47.2 | 50.3 | 1 | C6 |
| 36.5 | 41.6 | 2 | C1 |
| 29.6 | 35.3 | 2 | C7 |
| 24.6 | 28.7 | 2 | C12 |
| 24.4 | 24.9 | 4 | C13 |
| 23.6 | 25.1 | 2 | C8 |

Fourier Transform Infrared Spectroscopy (IR)

Figure 5:
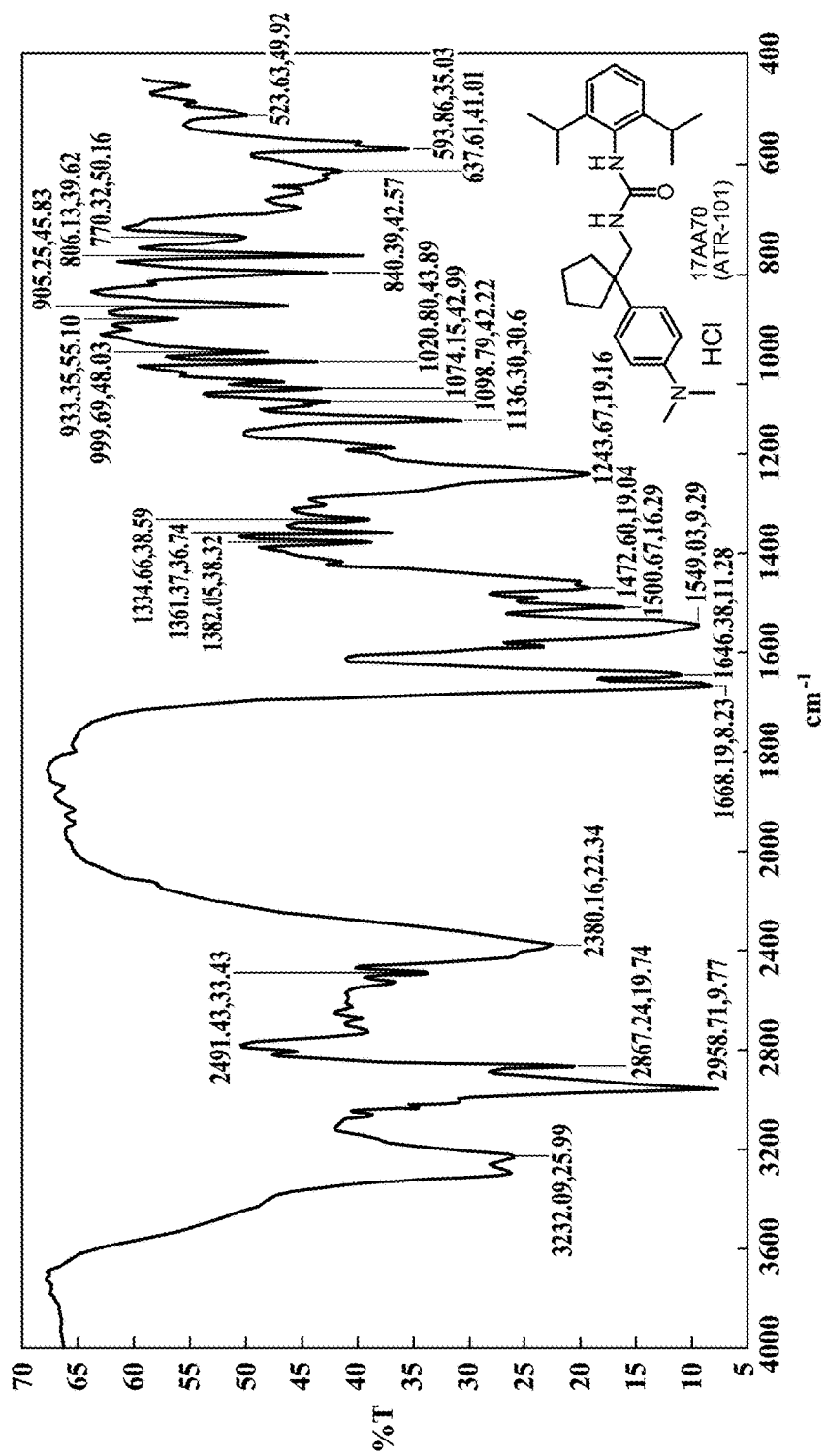
FIG. 5 is the FT-IR spectrum the solid drug form of ATR-101.

Infrared (IR) spectroscopy was performed using the solid drug form of ATR-101. The resulting spectrum, shown in FIG. 5, is consistent with the structure of ATR-101 drug substance. The major peak assignments are presented in Table 3.

TABLE 3

| Wave number (cm$^{-1}$) | Functional Group |
|---|---|
| 3232 | N—H (Urea) |
| 2959 | C—H Stretches |
| 2380 | Aniline-HCl |
| 1668 | C=O (Urea) |
| Region 1200-1600 | Aromatic |

Differential Scanning Calorimetry (DSC)

Figure 6:
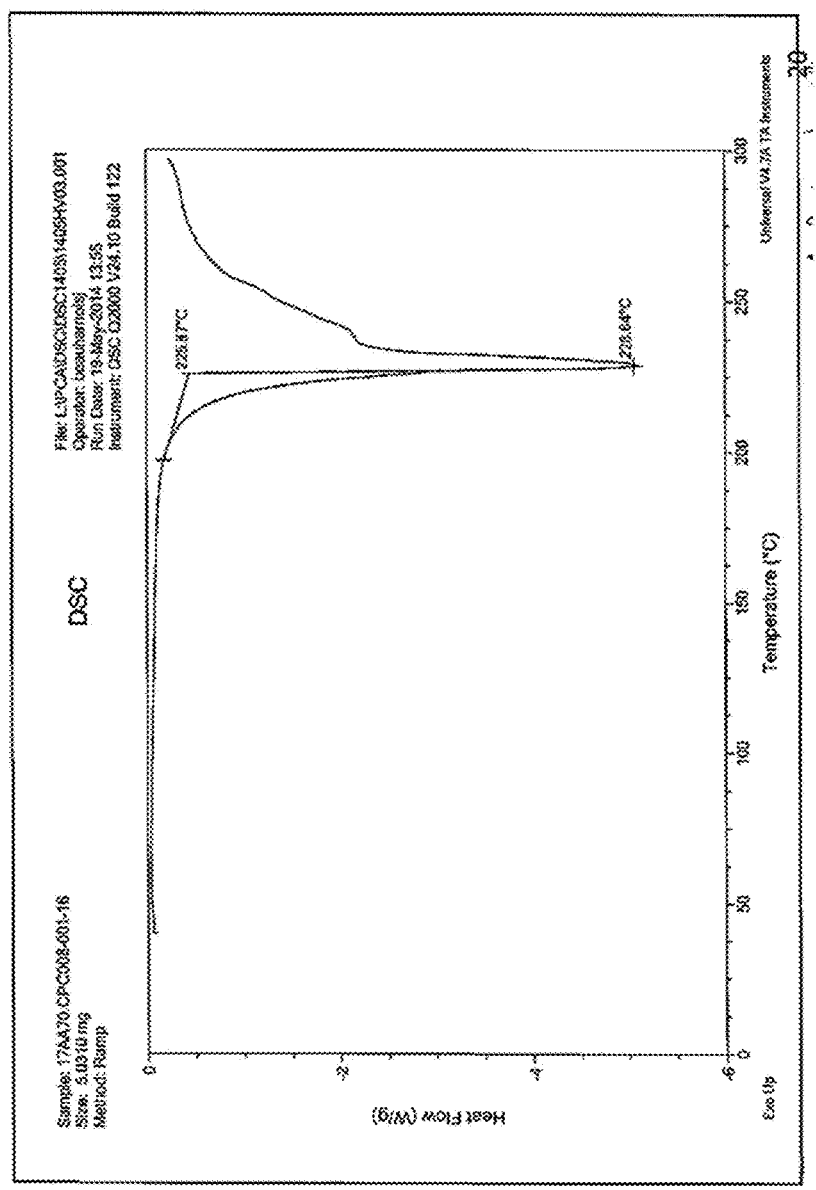
FIG. 6 is the DSC results for the solid drug form of ATR-101.

The DSC thermogram of the solid drug form of ATR-101 was obtained using a TA Instruments Q2000. A temperature ramp of 10° C./minute to 300° C. was used. An endothermic event was observed at 228.64° C. with an onset of 225.87° C. Results are shown in FIG. 6.

X-Ray Powder Diffraction Analysis (XRPD)

Figure 7:
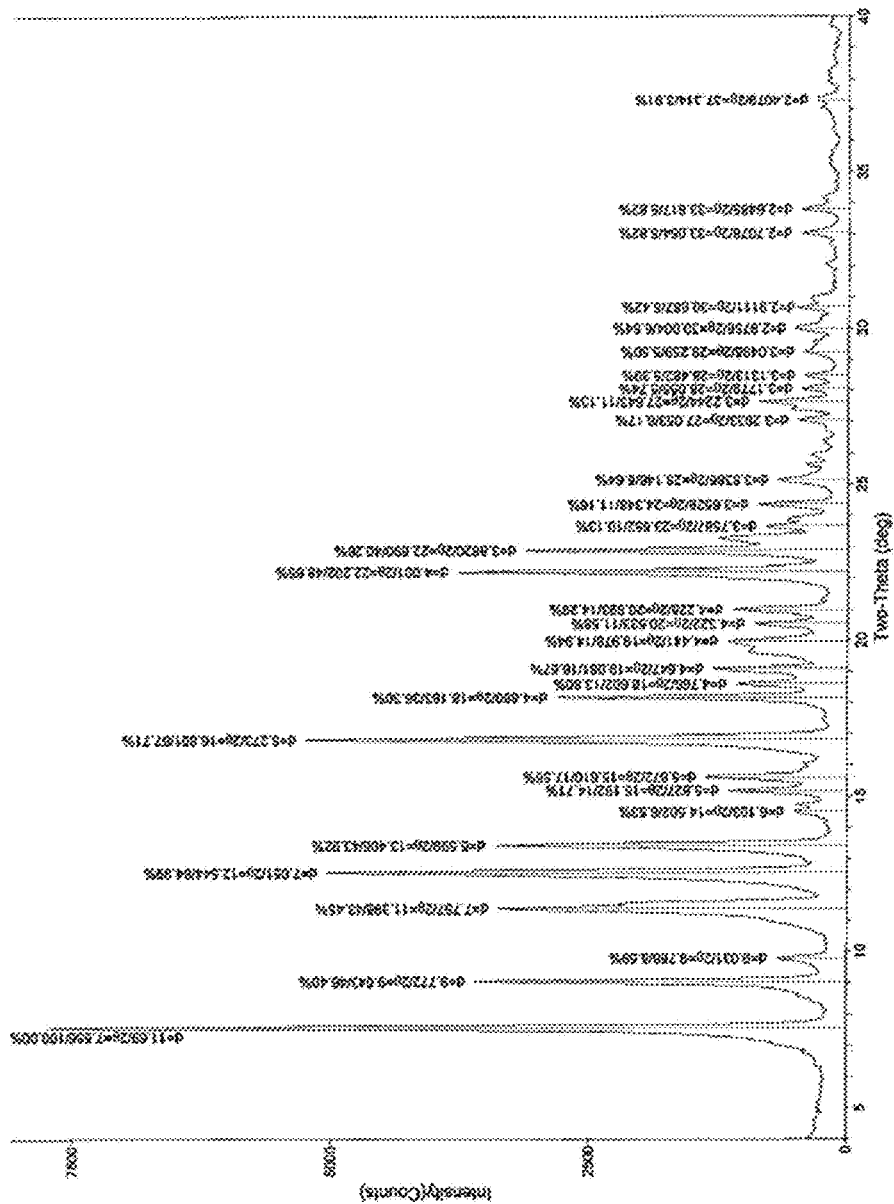
FIG. 7 is the XRPD diffraction of the solid drug form of ATR-101.

The X-Ray Powder Diffraction pattern of the solid drug form of ATR-101 was determined using a Siemens D500 Automated Powder Diffractometer equipped with a graphite monochromator and a Cu ($\lambda$=1.54 Å) X-ray source operated at 50 kV, 40 mA. The sample was analyzed using a measuring range of 4-40° 2$\Theta$, a step width of 0.050°, and a measuring time per step of 1.2 seconds. The resulting XRPD spectra, shown in FIG. 7, indicate that the sample is crystalline in nature.

Single Crystal X-Ray Diffraction

Figure 8:
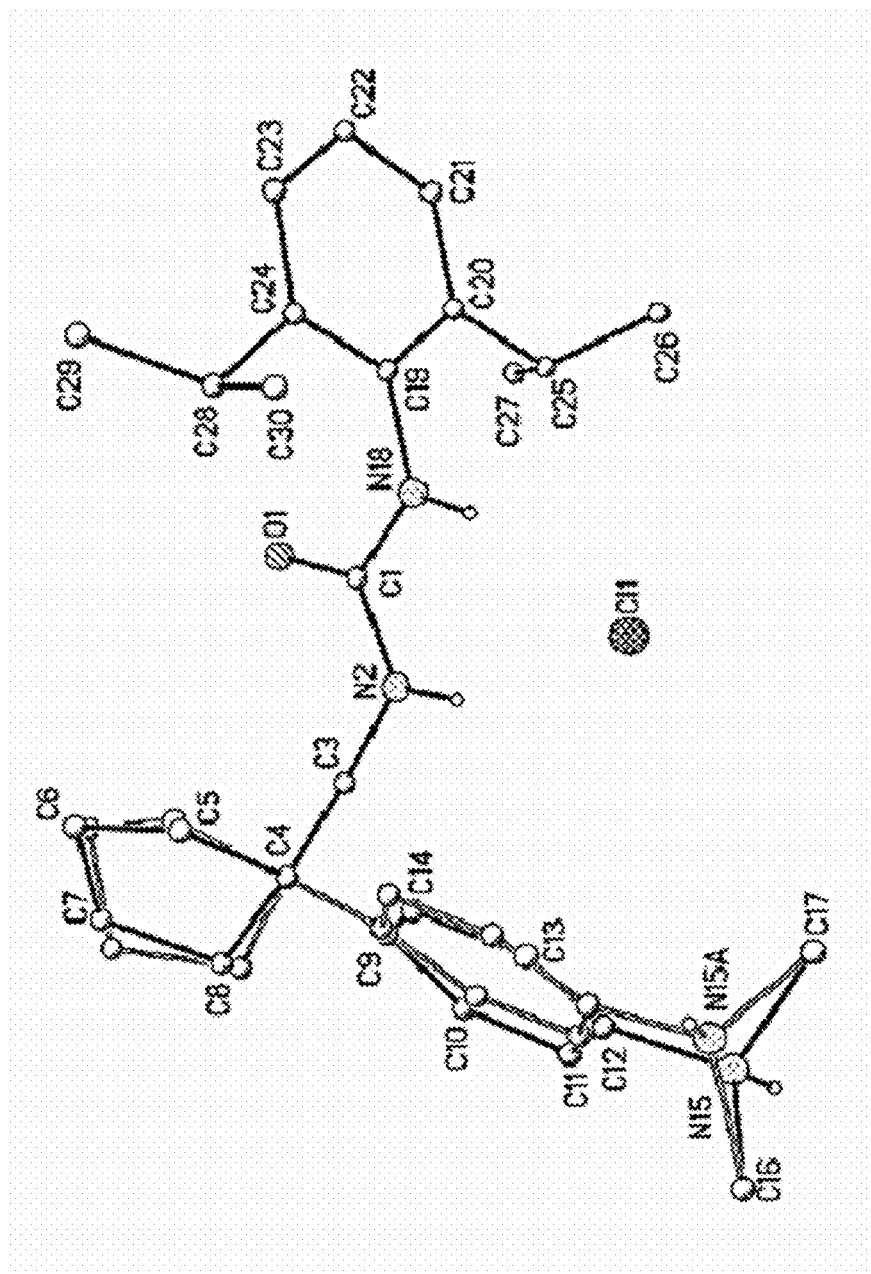
FIG. 8 is the superposition of both disorder components in the crystal structure of the solid drug form of ATR-101 (H atoms omitted for clarity).

Single crystal X-ray diffraction was a study carried out on the solid drug form of ATR-101 (Solid Form Solutions) on an Agilent Supernova dual sourced diffractometer equipped with an Oxford Cryosystem low-temperature device operating at 150 K. Data was collected using Cu-K$\alpha$ radiation ($\lambda$=1.54184 Å) to a resolution of 0.84 Å. Following integration and application of a multi-scan correction for systematic errors (CRYSALISPRO), data were merged in point group 2/m. The structure was solved by charge-flipping (SuperFlip) and refined by least squares against F2 using all data (ShelxL-2012). The single crystal structure, along with the superposition of a disorder component, is shown in FIG. 8.

Batch Analysis

Table 4 summarized the Batch Analysis Results for the solid drug form of ATR-101.

TABLE 4

| Parameter/Method | Result |
|---|---|
| Description | White to off-white solid |
| Identification (IR) | Conforms to reference standard |
| Identification (HPLC) | Conforms to reference standard |
| Assay (HPLC, % w/w) | 98.3% |
| Related Substances (HPLC, area %) | |
| n-propyl isomer | 0.3% |
| major unspecified impurity | 0.1% |
| Other unspecified impurities: | |
| RRT 0.93 | Less than 0.05% |
| RRT 1.66 | 0.1% |
| Total impurities | 0.4% |
| Chloride Content (Titration, % w/w) | 7.60% |
| Water Content (Coulometric Titration, % w/w) | 0.2% |
| Residue on Ignition (% w/w) | 0.0% |
| Heavy Metals (USP<231>) | Conforms |
| Residual Pd (ICP) | 1 ppm |
| Residual Solvents (GC) | |
| Dichloromethane | Not detected |
| Acetonitrile | Not detected |
| Tetrahydrofuran | Not detected |
| Acetone | 3837 ppm |
| tert-Butanol | Not detected |
| Methanol | Less than 173 ppm |
| Isopropanol | Less than 288 ppm |
| X-ray Powder Diffraction (XRPD) | Conforms to reference standard |
| Particle Size (Laser Diffraction, μm) | |
| d(0.1) | 2 μm |
| d(0.5) | 12 μm |
| d(0.9) | 49 μm |
| Differential Scanning Calorimetry (DSC, ° C.) | |
| Onset | 228.28° C. |
| Endotherm | 230.93° C. |
| Microbial Limits (USP <61>, Ph. Eur. 2.6.12) | |
| Total Aerobic Microbial Count (TAMC) | Less than 10 cfu/g |
| Total Yeast and Mold (TYMC) | Less than 10 cfu/g |
| Specified Microorganism (USP <62>, Ph. Eur. 2.6.13) | |
| *E. coli* | Conforms |

Example 3

Comparison with Prior Art Synthesis of ATR-101 (by Trivedi et al., J. Med. Chem. 37:1652-1659, 1994)

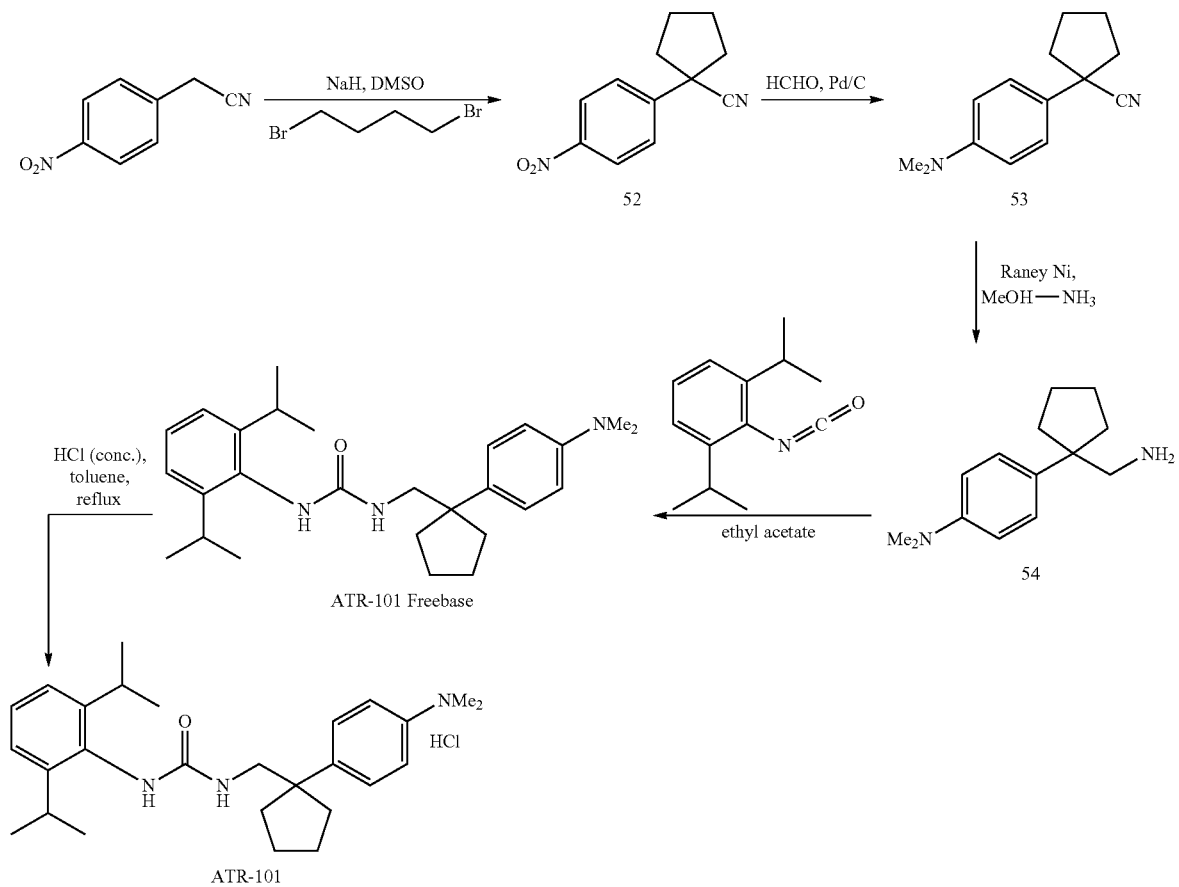

ATR-101 Freebase

ATR-101

In this experiment, 10.6 g of ATR-101 was synthesized according to the above procedure, which corresponds to the the procedure set forth in Trivedi et al., J. Med. Chem. 137:1652-1659, 1994 (hereinafter referred to as the "Trivedi procedure"). The purity of ATR-101 as made by the Trivedi procedure was found to be 94.9%, compared to a purity of 98.3% for ATR-101 obtained by the procedure of Example 1 and as evaluated in Example 2.

Step 1: Alkylation of p-nitrophenylacetonitrile

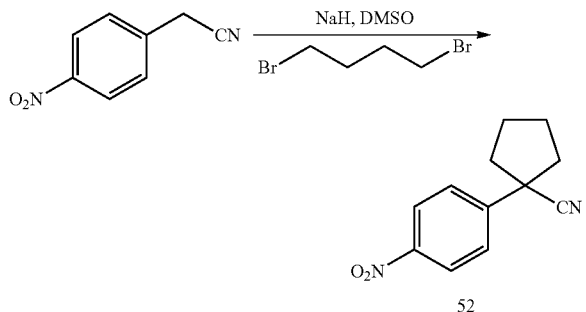

The initial alkylation reaction was run on 15.0 g scale and, according to the Trivedi procedure, should have given 15.7 g (79%) of product 52. However, several problems occurred, and the yield was much lower than expected (6.0 g, 30% yield), although the purity by 1H NMR and melting point (actual: 71-72° C., reported: 76° C.) seemed good. Approximately half way through the addition of 1,4-bromobutane and p-nitrophenylacetonitrile to NaH, a black solid precipitated out of the purple solution causing the stirbar in the flask to skip and jump. The rate of stirring had to be monitored throughout the remainder of the addition to maintain a sluggish and inefficient mixing of the solution.

After stirring at ambient temperature overnight to ensure reaction completion, the reaction was worked-up as the procedure indicated. First, excess ether was removed using air bubbling, and the black solid was isolated by filtration. Diethyl ether was then added until all of the solids dissolved to give a clear black solution. However, upon washing the ether solution with 2N HCl, a black amorphous solid precipitated from the solution. There was no note of this black solid in the Trivedi procedure, so the work-up was continued without modification. The black solids ended up in the aqueous washes, or stuck to the seperatory funnel. The remainder of the work-up proceeded as expected, and the hot hexanes extraction of the crude solid resulted in light pink planar crystals.

The procedure was repeated with two changes thought to be responsible for the low yield: the anhydrous solvent (from the bottle) was sieve dried to remove trace water, and the stir bar was replaced with a mechanical stirrer to ensure more even mixing of the solution. The procedure was re-run on 10 g scale, which should have yielded 10.5 g of compound 52. However, despite the changes to the procedure, the resulting product and yield was nearly identical to the first run (4.5 g, 34% yield, 71-72° C. melting point).

In an attempt to determine where the bulk of material ended up, the aqueous layer from this reaction was re-extracted with diethyl ether, but only resulted in trace amounts of material. The black solids that formed during the work-up were isolated by filtration, and an NMR was taken of the material. The NMR showed peaks corresponding to compound 52. Presumably, this amorphous black solid that resulted after HCl formation is the main source of lost material, as there appeared to be several grams of it.

Step 2: Reduction of Nitro Compound

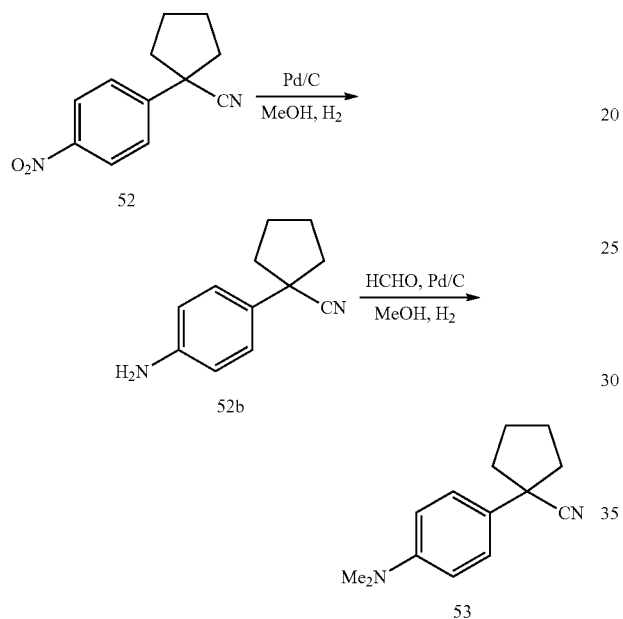

The conversion of nitro compound 52 to the dimethyl amine 53 was done over two steps: palladium catalyzed hydrogenation of the nitro compound to give the free amine 52b, followed by imine formation & reduction to the dimethylamine 53.

An exploratory small scale reaction was run, using 1/10th of the available material (1.0 g compound 52). The reduction of the nitro compound on the 1 gram scale was very rapid, with hydrogen consumption ceasing after 3-4 hours. A crude NMR of an aliquot of the reaction mixture showed very clean amine (52b). The formaldehyde was added, as well as additional Pd/C, and the hydrogenation was continued. The hydrogen was not consumed as quickly for the imine reduction, and the reaction was still progressing when the vessel was pressurized to 55 psi and left shaking overnight (ca. 16 h).

After 16 hours, the pressure in the flask had dropped to 30 psi, indicating that the hydrogenation was still progressing overnight. An aliquot NMR confirmed that the reaction had not proceeded to completion.

On large scale, the nitro reduction proceeded very smoothly, consuming hydrogen at a very rapid rate, and going to completion again within 3-4 hours. The reactor was pressurized to 55 psi and shaken overnight, as indicated in the original procedure, before more Pd/C was added, followed by formaldehyde. Hydrogen consumption was again observed to be very sluggish, so the valve to the hydrogen tank was left open to the vessel, and the reaction was shaken for 24 hours.

After 24 hours of shaking, the valve to the vessel was closed, and a drop of 5 psi was observed over 1 hour, indicating that the reaction had not progressed to completion. TLC also showed several polar products, suggesting that the reaction was only ca. 50% complete. The hydrogenation vessel was pressurized to 55 psi with hydrogen, and the valve again left open for an additional 24 hours of hydrogenation.

After 24 hours, the reaction stopped consuming hydrogen, and the vessel was purged and the contents filtered to remove the palladium catalyst. The work-up was performed similarly to the small scale, and the two reactions were combined prior to purification by column chromatography, giving 5.7 g (57.5% yield) of the desired dimethylamine product 53.

Step 3: Reduction of Cyano Compound

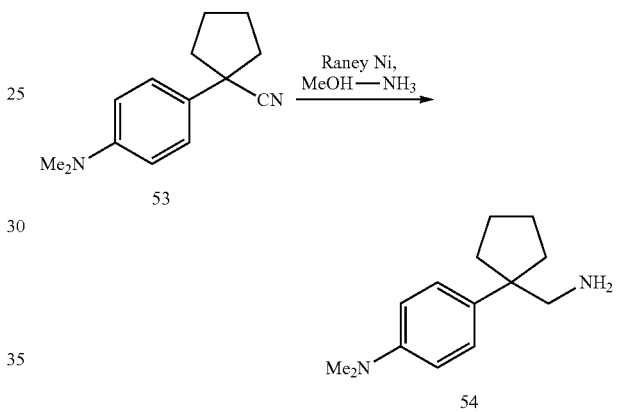

A small scale RaNi hydrogenation was done and the test reaction went smoothly. Hydrogen consumption was rapid, and the reaction appeared complete after approximately 2 hours. The consumption of hydrogen had ceased, and TLC indicated that there was no compound 53 remaining. After filtration to remove the Raney Nickel, the reaction completion was confirmed by aliquot NMR.

The remaining material was subjected to reduction using the same conditions, and hydrogen consumption and TLC analysis again indicated reaction completion after 2 hours. The material was filtered and combined with the smaller scale reaction material. After concentration to dryness, the crude yield was found to be 5.5 g (96.5% yield), which was very close to the reported yield (99%).

Step 4: Formation of Urea Compound

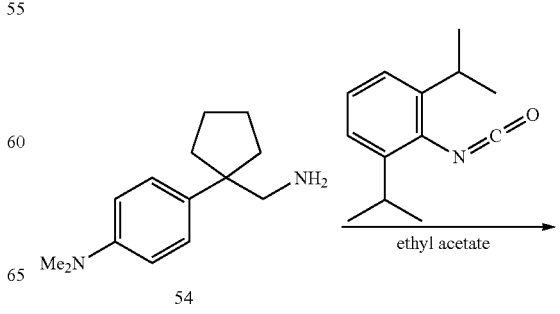

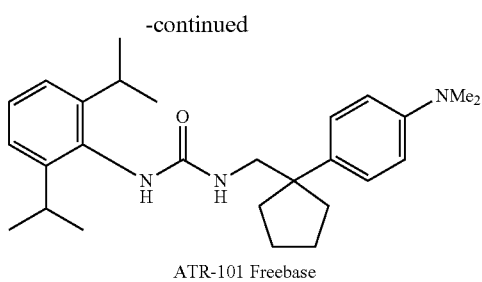

ATR-101 Freebase

Urea formation is a straightforward procedure, and the small scale test reaction with the amine 54 (500 mg) being combined with 1.0 equivalent of the isocyanate in 20 parts ethyl acetate. After stirring for 16 hours, the solution was concentrated to dryness to give a white solid. Crude 1H NMR of the solid confirmed that the spectra matched the reported spectra in the Trivedi procedure.

The remaining material was carried forward to ATR-101 freebase without difficulty, and the lots of product were combined. In an effort to remove the residual ethyl acetate, the solids were dissolved in 10 mL of toluene, followed by concentration under reduced pressure. After drying on high-vacuum, ATR-101 freebase was isolated as a sticky white foam (10.6 g, 99% yield). The 1H NMR of the final product showed trace toluene even after extended drying, and the material was moved on to the HCl salt formation.

The melting point of the solid was later taken and found to be surprisingly low (50-56° C., expected: 132-133° C.). The nature of the solid (oily foam) made the determination of the melting point difficult, but it was judged to be completely melted above 60° C.

Step 5: Formation of HCl Salt

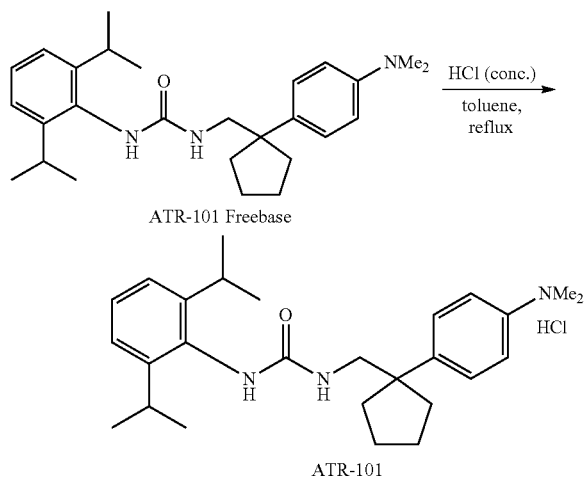

To the ATR-101 freebase in toluene was added 37% HCl, and a gummy white solid precipitated out immediately. The solution was dried by Dean-Stark apparatus over approximately 3 hours with vigorous stirring and heating (bath temp: 160° C.). After drying, the solution was cooled and the fine crystalline solid was isolated by filtration and washed with acetone and diethyl ether. The product ATR-101 was dried until a constant weight was achieved (10.6 g, 92% yield) and fully characterized.

SUMMARY

The Trivedi procedure was successfully repeated to synthesize 10.6 grams of ATR-101. The initial step in the process proved difficult, with a considerably lower yield that reported. The reduction of the nitro compound to the amine proceeded smoothly, but the methylation using formaldehyde and hydrogenation of the resulting imine was very sluggish, resulting in a lower than expected yield. The Raney Nickel reduction of the nitrile proceeded uneventfully, with the expected yield and purity of the resulting amine. The urea formation, and final HCl salt formation also proceeded smoothly to furnish ATR-101 in excellent yield over the last steps.

The purity of the ATR-101 synthesized via the Trivedi procedure was found to be 94.9% (see Table 5 below). Of particular note was the very high level of the 2-n-propyl-6-isopropyl isomer (RRT 1.02), as well as the 2,4-diisopropyl regioisomer (RRT 1.09).

TABLE 5

Analysis of ATR-101 Made by Trivedi Procedure

| RT | Identity | RRT | Area % |
|---|---|---|---|
| 5.18 | — | 0.24 | 0.093 |
| 19.985 | — | 0.93 | 0.329 |
| 20.129 | — | 0.94 | 0.38 |
| 20.806 | — | 0.97 | 0.058 |
| 21.376 | ATR-101 (HCl salt) | 1.00 | 94.858 |
| 21.757 | n-propyl-6-isopropyl isomer | 1.02 | 1.976 |
| 23.316 | 2,4-diisopropyl regioisomer | 1.09 | 2.005 |
| 30.891 | — | 1.45 | 0.092 |
| 31.517 | — | 1.47 | 0.052 |
| 32.24 | — | 1.51 | 0.072 |
| 35.292 | — | 1.65 | 0.086 |

Example 4

Large Sale Synthesis—Low Purity

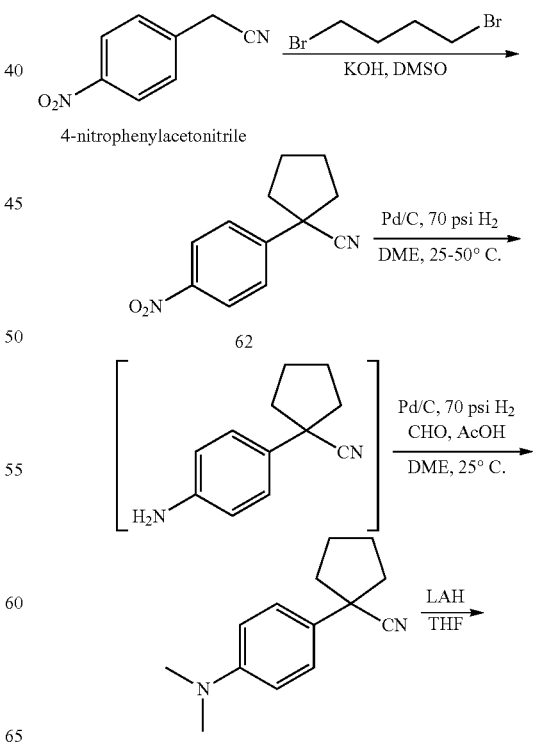

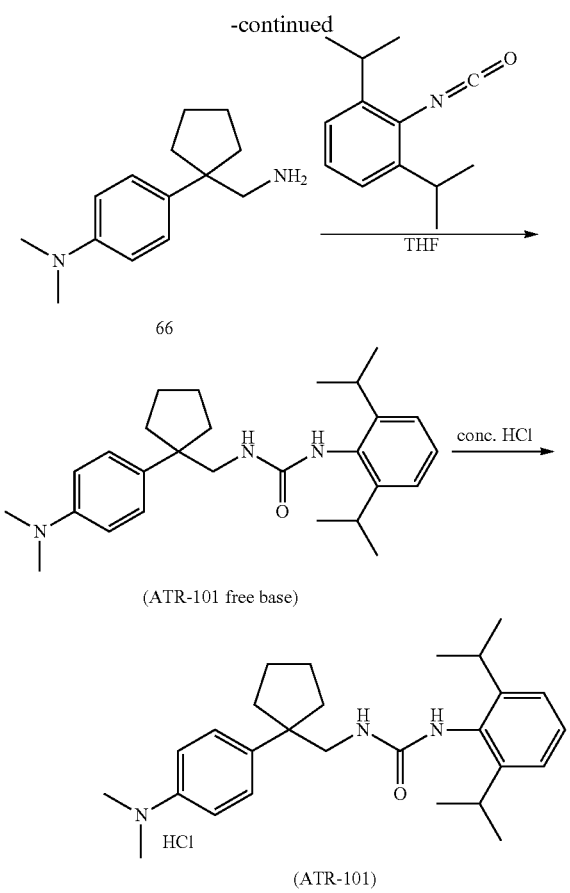

(ATR-101 free base)

(ATR-101)

Initial large scale synthesis was performed by the procedure depicted above. In the first step, 4-nitrophenylacetonitrile was alkylated with 1,4-dibromobutane to generate 62, this was carried out in DMSO with KOH as the base. The product (a dark-colored solid) was then isolated by first carrying out an aqueous workup using MTBE as the extraction solvent and then concentrating the solvent to dryness. Several batches were run on ~3 kg scale each to give yields ranging from 92-100% with purity ranging from 83-95%.

The second step effects the reduction of the nitro group to the corresponding aniline and subsequent double reductive amination with formaldehyde and AcOH to afford dimethylaniline 64. This was accomplished using a typical Pd/C catalyst with DME as the reaction solvent. Upon observing reaction completion, the catalyst was filtered and the product was obtained in crude form after an aqueous workup and concentration of the solvent to dryness. The crude solid was then purified by heating it in heptane to 80° C. (which affords a biphasic mixture) and decanting the clean upper phase from the lower "red sludge" phase. The heptane extract that was obtained in this manner was then concentrated to dryness. The resulting solid was then recrystallized from IPA/H2O before use in the next step. This sequence was carried out on 2.6 kg scale four times, and the crude materials were pooled together for the purification procedure described above; the product was obtained in 51% yield with 97.5% purity by HPLC.

The third step in the sequence is the reduction of the nitrile to the corresponding primary amine 66, this was by using LAH (sourced as pellets) in THF. After the reaction was complete, a typical "Fieser" quench was employed to convert the aluminum salts to a filterable form. After filtering off the aluminum salts, the product was then obtained as a solid by concentration of the filtrate to dryness. This was carried out on 500 g scale, and gave the product in 95% yield.

The fourth step of the process is the coupling of the amine 66 with 2,6-diisopropylphenyl isocyanate to give the free base of ATR-101. This was accomplished by adding the isocyanate (neat) to a suspension of 66 in THF. Once the reaction was complete, the THF was distilled down to a certain volume, acetone was added, and the product was precipitated by the addition of water. Filtration and drying then afforded 16AA70040. On a 300 g scale, this gave the product in 74% yield with 97.5% purity.

The final step of the process is the conversion of ATR-101 free base to the corresponding HCl salt (ATR-101). This was accomplished by adding conc. HCl to a slurry of the freebase in IPA (slurry-to-slurry conversion). The resulting slurry was concentrated to reduce the volume of IPA, and MTBE was added as the antisolvent. The product was then isolated by filtration to give crude ATR-101 in 94% yield (400 g scale). The material was subsequently recrystallized from MeOH/MTBE to afford the purified ATR-101 in 84% yield and with a purity of 99.7% (subsequently found to be incorrect) by HPLC.

However, it was later discovered that the batches produced by the above technique were contaminated with two isomeric impurities not resolved by HPLC; namely, the 2,4-diisopropyl regioisomer and the 2-n-propyl-6-isopropyl isomer:

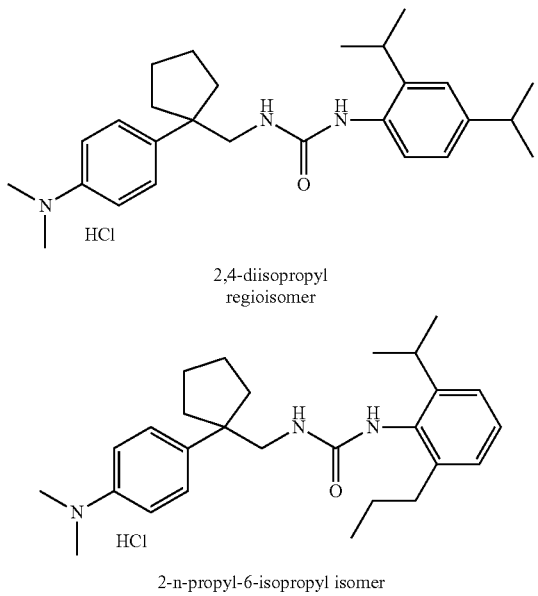

2,4-diisopropyl regioisomer 2-n-propyl-6-isopropyl isomer

Thus, despited believing that ATR-101 was obtained at a high level of purity, it was in fact produced at a much lower level of purity (i.e., less than 95%) due to the presence of the above impurities (these impurities were only discovered after manufacture when analyzed by more sensitive HPLC methods). Critically, it was found to be very difficult to purge these closely-related impurities from ATR-101.

Example 5

Large Sale Synthesis—High Purity

The procedure of Example 4 was found to have several drawbacks, most notably its failure to achieve ATR-101 at high purity. To avoid generation of the 2,4-diisopropyl regioisomer and the 2-n-propyl-6-isopropyl isomer, alternative preparation of the 2,6-diisopropylphenyl isocyanate from 2,6-diisopropylaniline was explored.

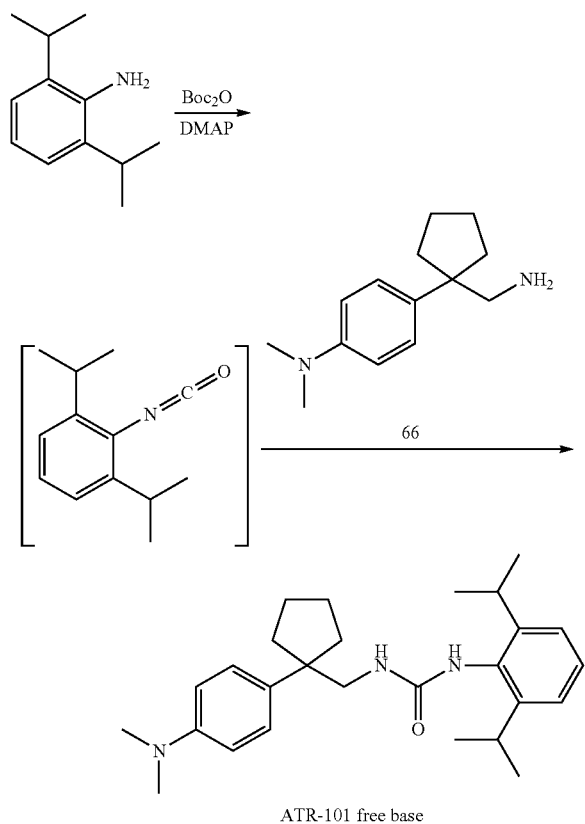

ATR-101 free base

A preliminary experiment was carried out in order to evaluate a literature procedure (Knolker et al., ACIEE, 34(22):2497-2500, 1995) for the preparation of isocyanates using Boc$_2$O (1.4 equiv) and DMAP (1.0 equiv) in MeCN. It was found that formation of the symmetrical urea (shown below) was problematic.

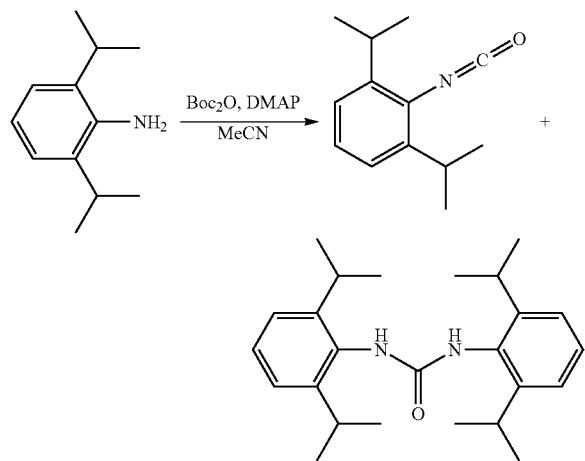

In this experiment, carrying out the reaction at room temperature led to exclusive formation of this impurity.

Further experiments (using 1.4 equiv Boc$_2$O and 1.0 equiv DMAP) revealed that formation of the symmetrical urea could be avoided by ensuring that the reaction temperature was maintained at 0° C. until isocyanate formation was complete. DCM was also found to be an acceptable solvent for generating the isocyanate, but the use of THF led to unacceptable amounts of the symmetrical urea, even when run at −20° C.

Because the isocyanate could be generated cleanly in an appropriate solvent, it was used as an intermediate generated in situ rather than as an isolated intermediate. (Note that this strategy requires that the 2,6-diisopropylaniline be purified prior to use as discussed below.) The viability of this approach was first demonstrated using MeCN as the reaction solvent. After generation of the isocyanate using the conditions described above, addition of 66 led to very clean conversion to ATR-101 free base. An aqueous workup could then be employed to remove residual DMAP.

In order to simplify the workup, further experiments were carried out using DCM as the reaction solvent (to avoid a reaction solvent that is miscible with water). After a short period of optimization, the stoichiometry of the Boc$_2$O was reduced to 1.05 equiv (to minimize adventitious formation of Boc-protected 66) and the amount of DMAP (which functions as a catalyst) was reduced to 10 mol %. Under these conditions, the principle reactants (2,6-diisopropylaniline and 66) could be employed in a 1:1 molar ratio.

It was also found that there was flexibility in the amount of solvent used for the reaction, as most of the reaction components (with the exception of 66) are highly soluble in DCM. In addition, the Boc$_2$O and aniline can be added neat or as DCM solutions. This allowed us easier tailoring of the reaction volumes to suit the equipment used in large scale production.

After obtaining optimized reaction conditions, attention was then focused on identifying appropriate conditions to isolate ATR-101 free base. A screen of solvents indicated that MeOH, IPA, and MeCN were all potential candidates for crystallizing ATR-101 free base. Crystallization was better yielding from IPA than MeOH, and mixtures using MeCN were found to be very thick, so IPA was ultimately selected as the crystallization solvent. Depending on the purity of the material, we anticipated that water could also be used as antisolvent to maximize recovery.

It was also discovered that it may be possible to avoid an aqueous workup altogether, since the quantity of DMAP being used in the reaction had been reduced to only 10 mol % and there should be no other byproducts to remove other than residual Boc$_2$O and t-BuOH. To this end, an experiment was carried out using DCM as reaction solvent and at the conclusion of the reaction, the reaction mixture was solvent-exchanged from DCM into IPA. Crystallization then occurred readily, and the product was isolated in 79% yield without contamination from residual DMAP.

With regard to the step of HCl salt formation, evaluation of IPA as the crystallization solvent for generating ATR-101 was undertaken. Although IPA gave yields above 90%, concerns about the possibility of forming isopropyl chloride led to evaluation of other solvent systems. THF, DMA and acetone were evaluated and all worked well, and acetone was selected as optimal because it is easy to dry, has a high ICH limit, and is inexpensive. In addition, the free-base can be dissolved readily in acetone and polish filtered prior to addition of HCl (in contrast to the procedure of Example 4 which was a slurry-to-slurry conversion).

The experiments described above utilized commercially available 2,6-diisopropylaniline, which has been found to contain unacceptably high levels of the undesired 2,4-diisopropyl regioisomer and the 2-n-propyl-6-isopropyl isomer. To address this problem, it was found that the commercially available material could be purified as its hydrochloride salt, and the isocyanate coupling could then employ aniline hydrochloride instead of the corresponding free base. This was accomplished by first free-basing the aniline hydrochloride in DCM/aqueous NaOH. The resulting DCM solution containing the purified 2,6-diisopropylaniline could then be distilled down to a volume appropriate for use in the isocyanate coupling. The distillation also served to ensure that the solution would be dry prior to use.

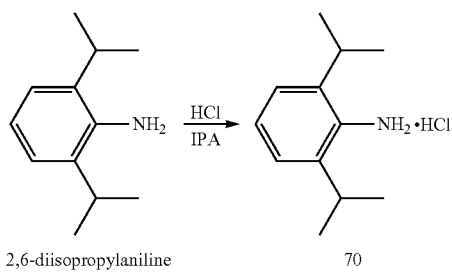

2,6-diisopropylaniline                    70

Because purification of 2,6-diisopropylphenyl isocyanate (an oil which was not readily available commercially) was not practicable, purification of the parent aniline via crystallization as the HCl salt was employed (see above scheme). Early experiments demonstrated that the desired hydrochloride salt 70 could be crystallized from IPA. Different polymorphic forms of this material were observed during the development work. It was found that addition of conc. HCl to a solution of the aniline at room temperature led to crystallization of product of one particular form. If this slurry was then heated to reflux (whereupon all or most of the material dissolved) and subsequently allowed to cool to room temperature, material of a different (and less soluble) polymorphic form was obtained. Importantly, the second polymorphic form appeared to crystallize with a higher purity than the first form.

In a demonstration experiment following this procedure, the desired 70 was obtained in 72% yield and in high purity (<0.2% of each of the undesired isomers) from 5 vols of IPA and 1.05 equiv of HCl. An MTBE wash of the product cake was incorporated in this experiment in order to facilitate drying of the product. One minor issue that was encountered, however, was that addition of the HCl to the solution of the aniline in IPA at room temperature led to the formation of an unacceptably thick mixture as the product crystallized. For this reason, scale up charged the HCl to a hot solution (60° C.) of the aniline in IPA. In this way, the reaction mixture would remain agitable.

In view of the above discoveries, the complete large-scale reaction scheme which yields ATR-101 in high purity follows:

Alkylation Step

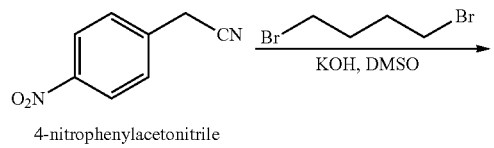

4-nitrophenylacetonitrile

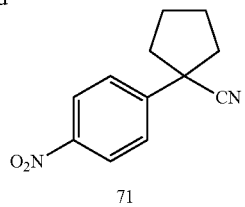

To a jacketed reactor vessel were charged KOH (flakes; 2.5 equiv) and DMSO (2.0 vols), giving a suspension. A solution of the nitrile (1.0 equiv) and 1,4-dibromobutane (1.05 equiv) was prepared in DMSO (3.5 vols) in a separate flask. This solution was then cannulated into the KOH suspension slowly over 4.5 h while maintaining the reaction temperature below 30° C. With a jacket temperature of 15° C., a maximum batch temperature of 27° C. was observed. After stirring overnight at 17-18° C., HPLC analysis of an aliquot indicated 5% nitrile remaining. The batch was warmed to 25-30° C. and an additional 5 mol % of 1,4-dibromobutane was added. After an additional hour, the amount of nitrile remaining was <3%, and so the reaction was deemed complete.

The reaction mixture was filtered to remove the inorganic materials, and the reactor and cake were washed with DMSO (1 vol). The batch was then worked-up in three equal portions. Each portion was charged to a clean jacketed reactor vessel and H₂O (13 vols) was then added slowly while maintaining the batch temperature below 30° C. (approximately 2 h with a jacket temperature of 10-15° C.). After aging for 2 h, the product was collected by filtration and the reactor and cake were washed with ice-cold 6:1 MeOH:H₂O (3.33 vols). Each portion was isolated in this fashion and then dried under vacuum at 40-45° C. to constant weight. This procedure gave the product 71 in a total 78.3% yield, with HPLC purity ~96% (with ~2% dimer impurity).

Hydrogenation Step

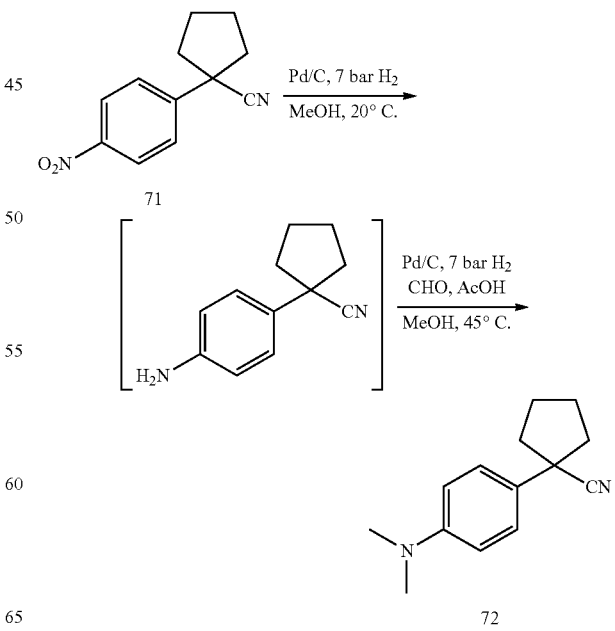

To a jacketed reactor were charged 71 (1.0 equiv), 10% Pd/C (7.0 wt %), and MeOH (10 vols). The contents of the reactor were inerted with $N_2$ and then pressurized with $H_2$ to 6.0 bar. The jacket was initially set to 18° C. to contain the minor exotherm that ensued. After 2 h, the jacket temperature was adjusted to 35° C. to achieve an acceptable reaction rate. The reaction mixture was stirred under these conditions overnight.

HPLC analysis of an aliquot of the reaction mixture revealed that conversion to the intermediate aniline was complete (<0.1% of the hydroxylamine intermediate remaining). To the reactor were then charged AcOH (1.0 equiv), formaldehyde (37% solution in MeOH, 2.7 equiv), and 10% Pd/C (3.0 wt %). The reaction mixture was again inerted with $N_2$ and then pressurized with $H_2$ to 6.0 bar and heated to 45° C.

After 2 h, HPLC analysis indicated that the reaction was complete (<0.1% monomethyl intermediate remaining). The reaction mixture was inerted with $N_2$ and then filtered through Celite while still at 45° C. The reactor and cake were washed with additional MeOH (2.0 vols), and the resulting filtrate was transferred to a clean jacketed reactor vessel. The solution was then distilled down to a level of 10 vols while maintaining a pot temperature of 40-50° C. (jacket temperature 55° C., 250 torr). This led to a homogenous solution at the conclusion of the distillation.

The solution was then cooled to 20° C. over 1 h. Crystallization began to occur at ~33° C. Water (5.0 vols) was then added dropwise over 1 h while maintaining the batch temperature at ~20° C. The resulting slurry was aged overnight and then filtered. The reactor and filter cake were washed with ice-cold 1:1 MeOH:$H_2O$ (5.0 vols). After drying under vacuum at 40-45° C. to constant weight, 72 was obtained in 90% yield with an HPLC purity of 96.0% (2.8% dimer-related impurity).

LAH Reduction Step

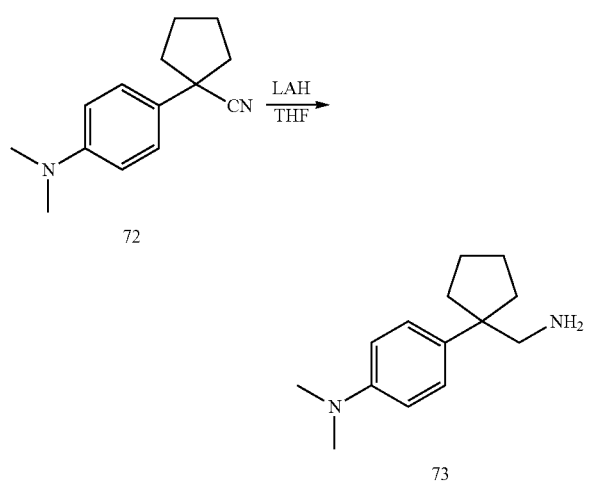

The starting material and THF (5.0 vols) were charged to a jacketed reactor vessel, resulting in a red/orange solution. LAH solution (2.4 M in THF, 1.5 equiv) was added over a period of 10 min, 1 and the resulting solution was then heated to 45° C. The reaction was found to be complete after 1.5 h (0.9% imine intermediate remaining). The reaction mixture was then cooled to 0° C. in preparation for the quench.

A solution comprised of 50% NaOH (1.5 equiv; 0.56 vols) and water (1.29 vols) was then added very slowly while maintaining the batch temperature at ~0° C. The addition required 1.5 h to complete and resulted in the formation of dense, granular solids. The reaction mixture was then warmed to 20° C. and filtered. Additional THF (2×3.5 vols) was used to wash the reactor and filter cake.

The filtrate was then transferred to a clean jacketed reactor and distilled under vacuum to a volume of 4 vols while maintaining a pot temperature of ~40° C. (jacket 50° C., 300 torr). MeCN (12 vols) was then charged, and the solution was again distilled under vacuum to a volume of 4 vols while maintaining a pot temperature of 50° C. Water (2.0 vols) was then added while maintaining the temperature at 50° C. The solution was then cooled to 40° C. and seeded (0.1 wt %). The reaction mixture was then cooled to 20° C. over 2 h. The mixture began to get quite thick with crystallized product at ~30° C.

Once the slurry had cooled to 20° C., additional water (4.0 vols) was added over 30 min while maintaining the batch temperature at 20° C. The slurry was then cooled to 0° C. over 1 h, aged for 1 h, and then filtered. The reactor and filter cake were washed with ice-cold 1:2 MeCN:$H_2O$ (3.0 vols). The product was then dried under vacuum at 40-45° C. to constant weight to afford an 85.0% yield of 73 with an HPLC purity of 97.2% (with 1.5% dimer-related impurity).

Isocyanate Coupling Step

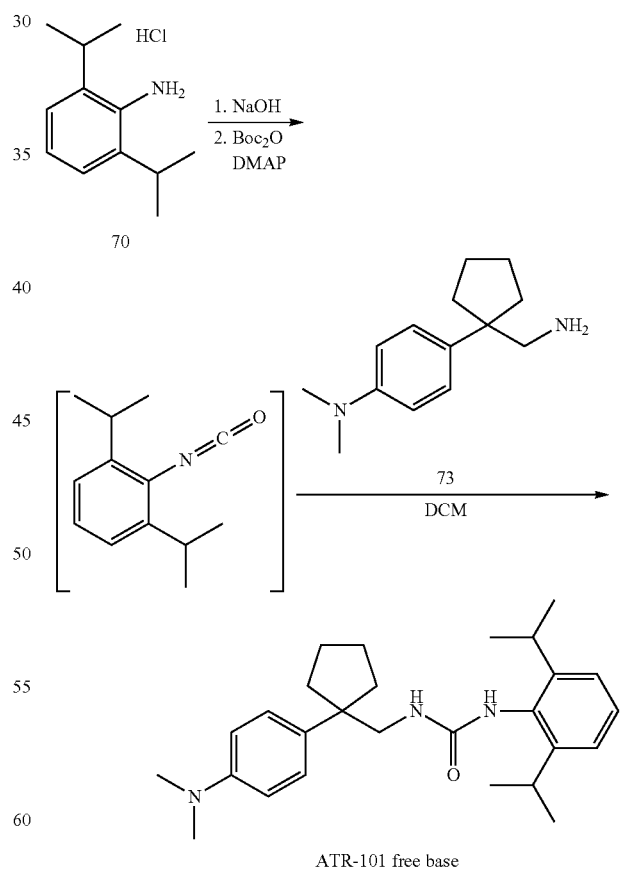

The aniline hydrochloride 70 (1.0 equiv) was converted to the corresponding freebase through an aqueous workup. The material was stirred in a mixture of DCM (5.0 vols) and 10% aq. NaOH (5.0 vols) for 30 min. The organic phase was separated and then washed with water (2×5.0 vols). The DCM solution containing the aniline freebase was then concentrated on the rotovap to a volume of 2.0 vols.

To a separate flask were then charged DMAP (10 mol %) and DCM (3 vols). The resulting solution was cooled to 0° C., and a solution of Boc$_2$O (1.05 equiv) in DCM (1.0 vol) was then added via cannula over 5-10 min while maintaining the batch temperature at 0° C. The aniline solution was then added via cannula over 30 min while maintaining the batch temperature at 0° C. After stirring for an additional 30 min, complete conversion to the isocyanate was observed by HPLC (0.6% aniline remaining).

To a separate flask was charged the 73 and DCM (3.0 vols). The resulting solution was then cooled to 0° C. and the isocyanate solution was added via cannula over 20 min while maintaining the temperature at 0° C. After 10 min, HPLC analysis indicated that the reaction was complete (0.3% 73 and 2.1% isocyanate remaining).

The reaction mixture was then distilled down to a volume of 5.0 vols under vacuum while maintaining the pot temperature at ~30° C. (40° jacket, 500 torr). IPA (22 vols) was then added, and the reaction mixture was distilled down to a volume of 20 vols under vacuum while maintaining a pot temperature of 50-60° C. (jacket 65° C., 350-200 torr). Once the distillation was complete, the solution was cooled to 40° C. and then seeded (0.1 wt %). The solution was then cooled to 20° C. over 1 h, and a thick slurry was obtained. H$_2$O (7.3 vols) was then added over 1.5 h while maintaining the batch temperature at 20° C. The resulting slurry was then cooled to 0° C., aged for 3 h, and then filtered. The reactor and filter cake were washed with ice-cold 1:1 IPA:H$_2$O (10 vols), and the product was dried under vacuum at 40-45° C. to constant weight. ATR-101 free base was obtained in 89% yield with an HPLC purity of 99.7%.

HCl Salt Preparation

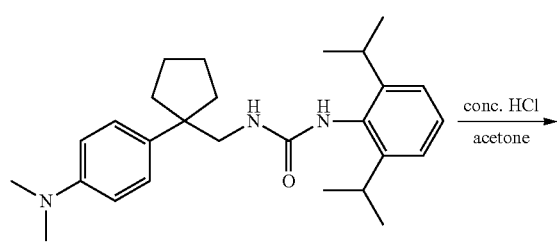

ATR-101 free base

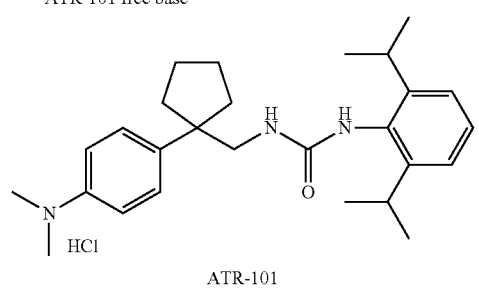

ATR-101

The free base was dissolved in acetone (7.0 vols) and polish filtered. Additional acetone (3.0 vols) was used to rinse the filter and transfer the solution to a reactor vessel. Conc. HCl (1.3 equiv) was then added over 10 min while maintaining the temperature at 20° C. Midway through the addition, the product began to crystallize. After the addition was complete, the resulting slurry was allowed to age for 2 h and was then filtered. The reactor and cake were washed with acetone (3.0 vols), and the product was then dried under vacuum at 40-45° C. to constant weight. After drying was complete, a 92.5% yield of ATR-101 with an HPLC purity of 99.7% was obtained.

Example 6

Preparation of Tablet Containing ATR-101

Tablets containing 500 mg ATR-101 (as the free base) may be prepared according to the procedure set forth below, and the make-up of exemplary tablets are listed in Tables 1 and 2.

A. High Shear Wet Granulation
1. ATR-101 is weighed.
2. Mannitol is weighed and passed through a No. 30 mesh screen.
3. Microcrystalline cellulose, croscarmellose, and pregelatinized starch are weighed and passed through a No. 30 mesh screen.
4. A pre-granulation mix of the intragranular excipients (components 2 and 3 above) and ATR-101 is prepared using a V-blender.
5. Hypromellose is weighed and dissolved in water under stirring.
6. The pregranulation mix is wet granulated with the hypromellose solution using a high shear granulator.
7. The wet granules are deagglomerated by passing through a No. 7 mesh screen. The granules are then dried in a fluid bed drier. The drying endpoint is determined by loss-on-drying (LOD).

B. Addition of Extragranular Excipients
1. The dried granules are passed through a No. 20 mesh screen and reintroduced into the V-blender.
2. Croscarmellose and magnesium stearate were are through a No. 30 mesh screen and added to the V-blender.
3. The dried granules and extragranular excipients are then mixed.

C. Compression
1. Tablet cores are compressed using a gravity fed rotary tablet press.

D. Film Coating
1. Core tablets maybe coated using a suitable coating solution.

TABLE 6

Ingredients of Representative 500 mg ATR-101 Tablet

| Ingredient | mg/tablet |
|---|---|
| ATR-101 (as free base) | 500 mg |
| Mannitol | 150 mg |
| Microcrystalline Cellulose Type 101 | 170 mg |
| Croscarmellose sodium | 20 mg |
| Pregelatinized starch | 50 mg |
| Hypromellose | 30 mg |
| Microcrystalline Cellulose Type 102 | 50 mg |
| Magnesium Stearate | 20 mg |
| Water (removed during processing) | — |

The following coated tablet was made in a similar manner as described above.

TABLE 7

Ingredients of Representative 500 mg ATR-101 Tablet

| Ingredient | mg/tablet |
| --- | --- |
| ATR-101 (as free base) | 500 mg |
| Mannitol | 54.3 mg |
| Microcrystalline Cellulose Type 101 | 54.3 mg |
| Croscarmellose sodium | 36.2 mg |
| Pregelatinized starch | 14.5 mg |
| Hypromellose | 14.5 mg |
| Magnesium Stearate | 7.2 mg |
| Opadry II White | 21.7 mg |
| Water (removed during processing) | — |

Example 7

Enhanced Exposure with Stomach Acidification

To examine pharmacokinetics and exposures of ATR-101 tablets prepared according to Example 6, an in vivo study was carried out in dogs following pretreatment with pentagastrin to decrease stomach pH, or famotidine to increase the stomach pH.

The same cohort of dogs was used in both treatments and included a 5-day wash-out between the treatment arms. Male beagle dogs (approximately 6.5-12.5 kg, n=6) were fasted overnight prior to dosing and through the first 4 hours of blood sample collection. For the pentagastrin arm, the animals were pretreated with a single intramuscular injection of pentagastrin (0.06 mg/mL at a dose level of 6 µg/kg and a dose volume of 0.01 mL/kg) 16 to 22 minutes prior to test article administration. For the famotidine arm, animals were pretreated with a single oral tablet dose of 20 mg famotidine at 59 to 60 minutes prior to tablet administration.

Following tablet administration, each animal received 30 mL of tap water via oral gavage. Animals were treated with a single 125 mg ATR-101 tablet by oral administration. The tablet was made as described in Example 6 above, and contained the ingredients listed in Table 6, but with the amount of ATR-101 at 125 mg (as free base) rather than 500 mg and the remaining ingredients reduced by the same weight percentage. PK blood samples for plasma were collected at 0 (predose), 1, 2, 4, 8 and 24 hours postdose for both treatment arms. Samples (~1 mL) were collected by jugular vein in K2EDTA-containing blood collection tubes, centrifuged under refrigerated (2 to 8° C.) conditions, plasma harvested and frozen at −60 to −90° C. ATR-101 concentrations were determined by LC/MSMS.

ATR-101 showed a 57% increase in systemic exposure in dogs pretreated with pentagastrin compared to pretreatment with famotidine demonstrating the benefit of an acidic stomach environment in the oral administration of ATR-101.

Example 8

Particle Size Study

Groups of ten jugular vein-cannulated female Sprague-Dawley rats approximately 13 weeks old with a targeted weight of 225 to 275 grams were administered single oral doses of various formulations of ATR-101 at approximately 3 mg/kg as indicated in Table 8. ATR-101 was administered in size 9 gelatin capsules (Groups 1-3) or by gavage (Group 4).

TABLE 8

Formulations

| Group No. | Description |
| --- | --- |
| 1 | 600-800 µm particle size |
| 2 | d(90) 18.5 µm particle size (sieved 270 mesh) |
| 3 | Micronized formulation (jet milling) 90% <5 µm particle size |
| 4 | Nano-milled formulation (nano colloidal dispersion) 90% <1 µm particle size |

Figure 9:
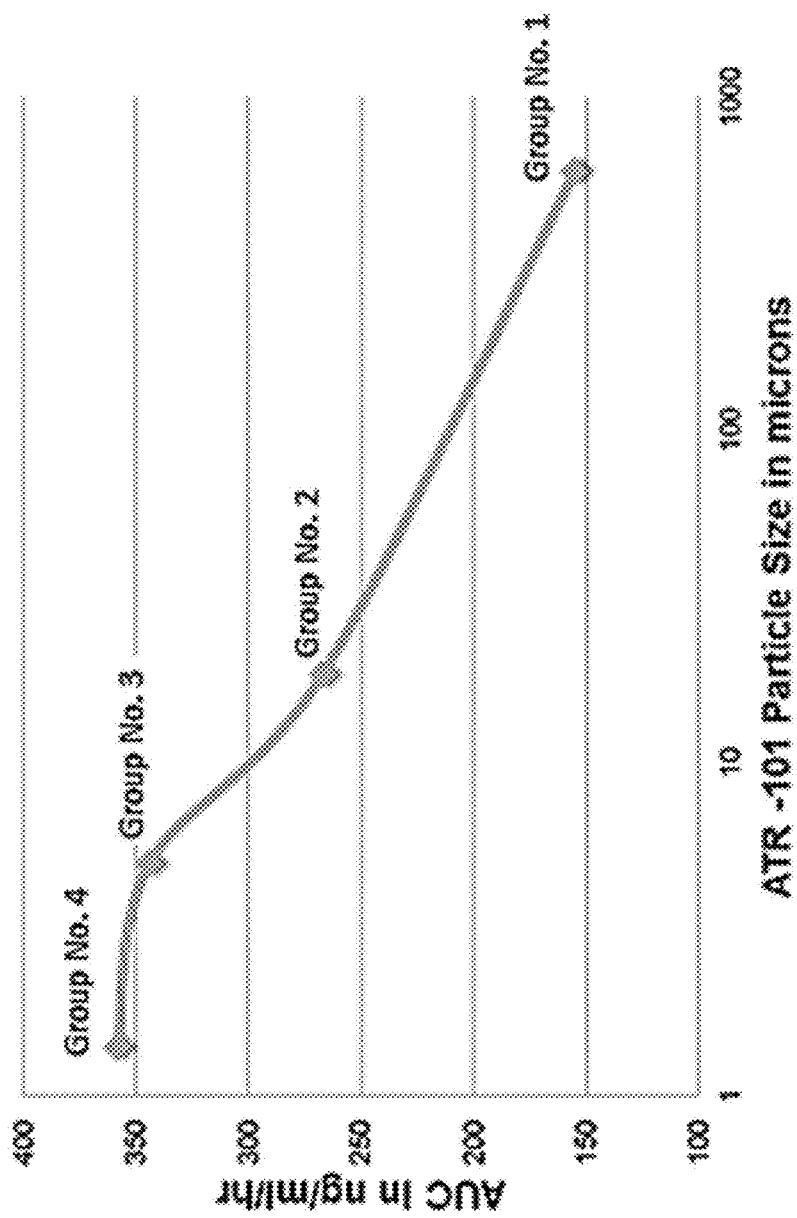
FIG. 9 is a graph showing exposure as a function of particle size.

Blood samples were collected 1, 2, 4, and 8 hours post dose in tubes containing K2EDTA. Table 9 shows the $C_{max}$ and exposures ($AUC_{0-24\ hr}$) achieved in rats for the different particle size formulations of ATR-101. As shown in FIG. 9, an increase in exposure was observed as the particle size decreased. The maximum exposure was achieved with formulations of particle size d (0.9)<5 µm. There was no further increase in exposure for the nano-milled formulation which had a particle size of d (0.9)<1 µm.

TABLE 9

$C_{max}$ and $AUC_{0-24}$ for Different Particle Sizes

| Group | $C_{max}$ (ng/mL) | $AUC_{0-24}$ (ng · hr/mL) |
| --- | --- | --- |
| 1 | 69.5 | 191 |
| 2 | 144 | 339 |
| 3 | 79.4 | 377 |
| 4 | 106 | 404 |

The formulations with smaller particle sizes showed increasingly difficult handling characteristics. The nano-milled formulations showed low bulk density and very poor flow character. Additional studies estimated that that the drug loading capacity of this formulation for tablets was about 25% whereas it was ~70% for the formulations with particle sizes of d (0.9)<18.5. The high (70%) drug loading capacity of this formulation is indeed surprising and suggests that the drug's physico-mechanical properties and/or surface properties lead to higher cohesion phenomenon.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way.

Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

The invention claimed is:

1. A solid drug form of N-(2,6-bis(1-methylethyl)phenyl)-N'-((1-(4-(dimethylamino)phenyl)cyclopentyl)methyl)urea hydrochloride having a purity in excess of 98% (w/w).

2. A solid drug form of claim 1 having a purity level in excess of 98.5% (w/w).

3. A solid drug form of claim 1 having a purity level in excess of 99% (w/w).

4. A solid pharmaceutical composition in a unit dosage form suitable for oral administration, comprising a solid drug form of claim 1 in combination with one or more pharmaceutically acceptable carriers or excipients.

5. A solid pharmaceutical composition in a unit dosage form suitable for oral administration, comprising a solid drug form of claim 2 in combination with one or more pharmaceutically acceptable carriers or excipients.

6. A solid pharmaceutical composition in a unit dosage form suitable for oral administration, comprising a solid drug form of claim 3 in combination with one or more pharmaceutically acceptable carriers or excipients.

* * * * *